(12) United States Patent
Sanders et al.

(10) Patent No.: US 7,622,299 B2
(45) Date of Patent: Nov. 24, 2009

(54) BIOENGINEERED TISSUE SUBSTITUTES

(75) Inventors: Joan E. Sanders, Kirkland, WA (US); Thomas Neumann, Seattle, WA (US)

(73) Assignee: University of Washington, Seattle, WA (US)

( * ) Notice: Subject to any disclaimer, the term of this patent is extended or adjusted under 35 U.S.C. 154(b) by 411 days.

(21) Appl. No.: 10/374,755

(22) Filed: Feb. 24, 2003

(65) Prior Publication Data

US 2003/0211130 A1 Nov. 13, 2003

Related U.S. Application Data

(60) Provisional application No. 60/359,470, filed on Feb. 22, 2002.

(51) Int. Cl.
*C12N 5/06* (2006.01)
(52) U.S. Cl. .......... 435/398; 435/395; 435/399; 435/402; 435/325; 623/1.1; 623/1.15; 623/1.22; 623/1.27; 623/2.1; 623/23.69; 623/23.7; 623/23.72; 623/23.76
(58) Field of Classification Search .......... None
See application file for complete search history.

(56) References Cited

U.S. PATENT DOCUMENTS

| | | | |
|---|---|---|---|
| 4,878,908 A * | 11/1989 | Martin et al. | 623/1.54 |
| 5,855,610 A | 1/1999 | Vacanti et al. | |
| 6,106,913 A | 8/2000 | Scardino et al. | |
| 6,308,509 B1 | 10/2001 | Scardino et al. | |
| 6,348,069 B1 | 2/2002 | Vacanti et al. | |
| 6,416,995 B1 | 7/2002 | Wolfinbarger | |
| 6,432,712 B1 | 8/2002 | Wolfinbarger, Jr. | |
| 6,455,311 B1 * | 9/2002 | Vacanti | 435/395 |
| 6,503,273 B1 | 1/2003 | McAllister et al. | |
| 6,537,567 B1 * | 3/2003 | Niklason et al. | 424/423 |
| 6,592,623 B1 * | 7/2003 | Bowlin et al. | 623/14.13 |
| 2002/0188349 A1 | 12/2002 | McAllister et al. | |
| 2003/0003153 A1 | 1/2003 | Asculai et al. | |

OTHER PUBLICATIONS

Doi et al, "Novel compliant and tissue-permeable microporous polyurethane vascular prosthesis fabricated using an excimer laser ablation technique" Journal of Biomedical Material Research, 1996, vol. 31, pp. 27-33.*

(Continued)

*Primary Examiner*—Allison M. Ford
(74) *Attorney, Agent, or Firm*—Christensen O'Connor Johnson Kindness PLLC

(57) ABSTRACT

In one aspect, the invention provides methods for forming a target tissue substitute. The methods of the invention comprise the following steps: (a) providing a scaffold comprising one or more layers of one or more arrays of microfibers, wherein one or more of the arrays of microfibers is designed to mimic the configuration of one or more structural elements in a target tissue; and (b) culturing cells on the scaffold to form a target tissue substitute. In another aspect, the invention provides implantable medical devices. The implantable medical devices of the invention comprise a scaffold comprising one or more layers of one or more arrays of microfibers, wherein one or more of the arrays of microfibers is arranged to mimic the configuration of one or more structural elements in a target tissue. Typically, cells are cultured on the scaffold to form a target tissue substitute.

69 Claims, 12 Drawing Sheets

OTHER PUBLICATIONS

Hayashi, K., "Experimental Approaches on Measuring the Mechanical Properties and Constitutive Laws of Arterial Walls," *Journal of Biomechanical Engineering 115*:481-488, Nov. 1993.

Sato, M., et al., "Axial Mechanical Properties of Arterial Walls and Their Anisotropy," *Medical & Biological Engineering & Computing 17*(2):170-176, Mar. 1979.

Segurola, et al., "Letter to the Editor: Strain-Induced Dual Alignment of L6 Rat Skeletal Muscle Cells," *In Vitro Cellular & Developmental Biology 34*:609-612, Jun. 1998.

Vandenburgh, H.H. et al., "Computer-Aided Mechanogenesis of Skeletal Muscle Organs From Single Cells In Vitro," *FASEB Journal 5*(13):2860-2867, Oct. 1991.

Conklin, B.S., et al., "A Simple Physiologic Pulsatile Perfusion System for the Study of Intact Vascular Tissue," *Medical Engineering & Physics 22*:441-449, 2000.

Doi, K., and T. Matsuda, "Significance of Porosity and Compliance of Microporous, Polyurethane-Based Microarterial Vessel on Neoarterial Wall Regeneration," *J. Biomed. Mater. Res. 37*:573-584, 1997.

Doi, K., and T. Matsuda, "Enhanced Vascularization in a Microporous Polyurethane Graft Impregnated With Basic Fibroblast Growth Factor and Heparin," *J. Biomed. Mater. Res. 34*:361-370, 1997.

Edelman, E.R., "Vascular Tissue Engineering: Designer Arteries," *Circulation Research 85*:1115-1117, 1999.

Hoerstrup, S.P., et al., "A New Approach to Completely Autologous Cardiovascular Tissue in Humans," *ASAIO Journal 48*:234-238, 2002.

Leor, J., et al., "Bioengineered Cardiac Grafts: A New Approach to Repair the Infarcted Myocardium?" *Circulation 102[suppl III]*:III-56-III-61, 2000.

L'Heureux, N., et al., "A Completely Biological Tissue-Engineered Human Blood Vessel," *FASEB Journal 12*:47-56, 1998.

McVeigh, G.E., et al., "Evaluation of Mechanical Arterial Properties: Clinical, Experimental and Therapeutic Aspects," *Clinical Science 102*:51-67, 2002.

Nerem, R.M., and D. Seliktar, "Vascular Tissue Engineering," *Annu. Rev. Biomed. Eng. 3*:225-243, 2001.

Niklason, L.E., et al., "Functional Arteries Grown In Vitro," *Science 284*:489-493, 1999.

Peng, X., et al., "In Vitro System to Study Realistic Pulsatile Flow and Stretch Signaling in Cultured Vascular Cells," *Am. J. Physiol. Cell Physiol. 279*:C797-C805, 2000.

Powell, C.A., "Mechanical Stimulation Improves Tissue-Engineered Human Skeletal Muscle," *Am. J. Physiol. Cell Physiol. 283*:C1557-C1565, 2002.

Ratcliffe, A., "Tissue Engineering of Vascular Grafts," *Matrix Biology 19*:353-357, 2000.

Sanders, J.E., et al., "Tissue Response to Single-Polymer Fibers of Varying Diameters: Evaluation of Fibrous Encapsulation and Macrophage Density," *J. Biomed. Mater. Res. 52*:231-237, 2000.

Sanders, J.E., et al., "Tissue Response to Microfibers of Different Polymers: Polyester, Polyethylene, Polylatic Acid, and Polyurethane," *J. Biomed. Mater. Res. 62*(2):222-227, 2002.

Seifalian, A.M., et al., "Improving the Clinical Patency of Prosthetic Vascular and Coronary Bypass Grafts: The Role of Seeding and Tissue Engineering," *Artificial Organs 26*(4):307-320, 2002.

Seliktar, D., "Dynamic Mechanical Conditioning of Collagen-Gel Blood Vessel Constructs Induces Remodeling In Vitro," *Annals of Biomedical Engineering 28*:351-362, 2000.

Shum-Tim, D., et al., "Tissue Engineering of Autologous Aorta Using a New Biodegradable Polymer," *Ann. Thorac. Surg. 68*:2298-2305, 1999.

Sieminski, A.L., and K.J. Gooch, "Biomaterial-Microvasculature Interactions," *Biomaterials 21*:2233-2241, 2000.

\* cited by examiner

Polymer fibers

BIOENGINEERED TISSUE SUBSTITUTES

CROSS-REFERENCE TO RELATED APPLICATION

This application claims the benefit of Provisional Application No. 60/359,470, filed Feb. 22, 2002, under 35 U.S.C. § 119.

GOVERNMENT RIGHTS

This invention was made with government support under R24HL064387 and RO1HD38554 awarded by the National Institutes of Health, and under EEC-9529161 awarded by the National Science Foundation. The government has certain rights in the invention.

FIELD OF THE INVENTION

The present invention relates to bioengineered tissue substitutes, such as blood vessel substitutes and muscle substitutes, and methods for forming bioengineered tissue substitutes.

BACKGROUND OF THE INVENTION

The repair and replacement of diseased tissue structures and organs requires an enormous expenditure of health-care resources. For example, approximately 500,000 coronary artery bypass surgeries are performed each year in the United States. The most common treatment, replacement with an autograft, produces less than optimal results—a graft patency of approximately 50-70% at 10 years with accelerated graft closure over time (Nerem et al. (1997) *Tissue Engineering and the Vascular System: Synthetic Biodegradable Polymer Scaffolds* (eds. Atala & Mooney) Boston, Birkhauser, pp. 165-85). While there are numerous prosthetic products in use, these also have limited lifetimes and elicit many unfavorable reactions in the body.

Accordingly, there is a need for bioengineered tissue substitutes, such as blood vessel substitutes and muscle substitutes, that can be custom-engineered to match the biomechanical, biochemical, and biological needs of the specific tissue or organ they are designed to replace.

SUMMARY OF THE INVENTION

In one aspect, the invention provides methods for forming a target tissue substitute. The methods of the invention comprise the following steps: (a) providing a scaffold comprising one or more layers of one or more arrays of microfibers, wherein one or more of the arrays of microfibers is designed to mimic the configuration of one or more structural elements in a target tissue; and (b) culturing cells on the scaffold to form a target tissue substitute.

The microfibers may have a diameter between about 1 micrometer and about 20 micrometers (such as between about 1 and about 15 micrometers or between about 1 micrometers and about 6 micrometers). In some embodiments, the microfibers are made of a biodegradable material that gradually transfers load from the scaffold to the target tissue substitute. Exemplary biodegradable materials are poly-L-lactic acid/polycaprolactone co-polymers, poly-caprolactone/poly-caprolactone-co-glycolide/poly-hydroxybutyrate-co-hydroxyvalerate/urethane co-polymers, degradable polyurethane, and polyglycolic acid.

The microfibers in an array typically have a regular spacing. The spacing between adjacent microfibers in an array may be between about 10 micrometers and 100 micrometers (such as between about 30 micrometers and about 70 micrometers or about 40 micrometers and about 60 micrometers).

The one or more arrays of microfibers in the scaffold may be arranged in one or more layers. The layers typically are regularly spaced. The spacing between the layers may be between about 10 micrometers and 200 micrometers (such as between about 60 micrometers and about 160 micrometers or between about 80 micrometers and about 120 micrometers). The microfibers in the scaffold may further comprise a coating comprising a cell adhesion-enhancing agent that promotes adhesion of cells to the scaffold and cell spreading. Illustrative cell adhesion-enhancing agents include, for example, fibronectin, laminin, and collagen.

Cells are cultured on the scaffold to form a target tissue substitute. In some embodiments, the cells may be cultured on the microfiber scaffold in the presence of dynamic mechanical conditioning.

In one illustrative embodiment of the invention, the target tissue may be an arterial blood vessel. According to this embodiment, an array of microfibers in the scaffold is designed to mimic the configuration of elastin in the medial layer of an arterial blood vessel. Thus, the scaffold may be a tubular scaffold comprising one or more layers of a helical array of regularly-spaced microfibers. In some embodiments, the scaffold for a blood vessel substitute comprises between 2 and 25 layers of microfibers (such as between 3 and 10 layers). Cells are cultured on the microfiber scaffold to form a blood vessel substitute. Typically, the cells cultured on scaffolds for forming a blood vessel substitute comprise smooth muscle cells. The blood vessel substitutes of the invention may further comprise endothelial cells. In some embodiments, the methods provide blood vessel substitutes, formed using three layers of microfibers, that exhibit a burst pressure of more than 1500 mm Hg after 2 weeks of culture in the absence of mechanical conditioning. In some embodiments, the burst pressure of the blood vessel substitutes produced according to the methods of the invention is more than 3000 mm Hg.

In another illustrative embodiment, the target tissue may be a muscle tissue, such as skeletal muscle tissue or cardiac muscle tissue. According to this embodiment, an array of microfibers is designed to mimic the configuration of muscle fibers in the muscle tissue. For example, in methods for forming a skeletal muscle substitute, an array of microfibers is designed to mimic the configuration of muscle fibers in skeletal muscle tissue. Similarly, in methods for forming a cardiac muscle substitute, an array of microfibers is designed to mimic the configuration of muscle fibers in cardiac muscle tissue.

Thus, the scaffold may comprise one or more layers of one or more linear, parallel arrays of microfibers having a regular spacing. The scaffold may have between 1 and 20 layers (such as between 5 and 10 layers). Cells are cultured on the microfiber scaffold to form a muscle substitute. Typically, the cells cultured on scaffolds for forming a skeletal muscle substitute comprise skeletal muscle cells, for example myoblasts. The cells cultured on scaffolds for forming a cardiac muscle substitute comprise cardial cells, for example cardiac muscle cells. The cells cultured on scaffolds for forming a muscle substitute may further comprise fibroblast cells.

In yet other embodiments, the methods of the invention can be applied to bioengineer tissue substitutes for other target tissues and organs in the body, including but not limited to, spinal cord, nerves, bone, cartilage, ligaments, tendons, heart valves, esophagus, cervix, bladder, skin, fascia, and other tissues. The methods comprise (a) providing a scaffold comprising one or more arrays of controlled-diameter microfibers, wherein at least one of the arrays is designed to mimic the configuration of one or more structural elements in the target tissue; and (b) culturing cells on the scaffold. For example, in a method for forming an esophagus substitute, the scaffold may comprise at least two layers of at least two arrays of microfibers, wherein a first array of microfibers is designed to mimic the configuration of the muscle fibers in the longitudinal muscle layer in the muscularis externa of the esophagus and a second array of microfibers is designed to mimic the configuration of the muscle fibers in the circumferential muscle layer in the muscularis externa. Cells are cultured on the microfiber scaffold to form an esophagus substitute. Typically, the cells cultured on scaffolds for forming an esophagus substitute comprise muscle cells.

In an illustrative embodiment of a method for forming a cartilage substitute, the scaffold may comprise one or more layers of one or more arrays of microfibers, wherein the array of microfibers is designed to mimic the configuration of collagen fibers in fibrous cartilage tissue. Cells are cultured on this scaffold to form a cartilage substitute. Typically, the cells cultured on scaffolds for forming a cartilage substitute comprise chondrocytes. The cells in this embodiment may further comprise fibroblasts.

In an illustrative embodiment of a method for forming a mitral heart valve, the scaffold may comprise one or more layers of a plurality of arrays of microfibers, wherein the plurality of arrays of microfibers is designed to mimic the configuration of collagen fibers in the mitral heart valve. Cells, such as interstitial valvular cells, fibroblasts, smooth muscle cells, and endothelial cells, are cultured on this microfiber scaffold to form an mitral heart valve substitute.

In another aspect, the invention provides implantable medical devices. The implantable medical devices of the invention comprise a scaffold comprising one or more layers of one or more arrays of microfibers, wherein one or more of the arrays of microfibers is arranged to mimic the configuration of one or more structural elements in a target tissue. Typically, cells are cultured on the scaffold to form a target tissue substitute.

The microfibers typically have a diameter between about 1 micrometer and about 20 micrometer (such as between about 1 micrometers and about 15 micrometers or between about 1 micrometers and about 6 micrometers). In some embodiments, the microfibers are made of a biodegradable material that gradually transfers load from the scaffold to the target tissue substitute. Exemplary biodegradable materials are poly-L-lactic acid/polycaprolactone co-polymers, poly-caprolactone/poly-caprolactone-co-glycolide/poly-hydroxybutyrate-co-hydroxyvalerate/urethane co-polymers, degradable polyurethane, and polyglycolic acid.

The microfibers in an array typically have a regular spacing. The spacing between adjacent microfibers in an array may be between about 10 micrometers and 100 micrometers (such as between about 30 micrometers and about 70 micrometers or about 40 micrometers and about 60 micrometers).

The one or more arrays of microfibers in the scaffold may be arranged in one or more layers. The layers typically are regularly spaced. The spacing between the layers may be between about 10 micrometers and 200 micrometers (such as between about 60 micrometers and about 160 micrometers or between about 80 micrometers and about 120 micrometers). The microfibers scaffold may further comprise a coating comprising a cell adhesion-enhancing agent to promote the adhesion and spreading of cells. Illustrative cell adhesion-enhancing agents include, for example, fibronectin, laminin, and collagen. Cells are cultured on the scaffold to form a target tissue substitute.

In one illustrative embodiment, the implantable medical device may comprise a scaffold for forming a blood vessel substitute. According to this embodiment, an array of microfibers in the scaffold is arranged to mimic the configuration of elastin in the medial layer of an arterial blood vessel. Thus, the scaffold may be a tubular scaffold comprising one or more layers of a helical array of regularly-spaced microfibers. In some embodiments, the scaffold for a blood vessel substitute comprises between 2 and 25 layers (such as between 3 and 10 layers). In some embodiments, the medical devices comprising a scaffold for forming a blood vessel substitute further comprise cells cultured on the scaffold to form a blood vessel substitute. The cells cultured on a scaffold for a blood vessel substitute may comprise smooth muscle cells. The blood vessel substitutes of the invention may further comprise endothelial cells. In some embodiments, the implantable medical devices comprise blood vessel substitutes, formed using three layers of microfibers, that exhibit a burst pressure of more than 1500 mm Hg after 2 weeks of culture in the absence of mechanical conditioning. In some embodiments, the implantable medical devices of the invention comprise blood vessel substitutes exhibiting a burst pressure of more than 3000 mm Hg.

In another illustrative embodiment, the implantable medical device may comprise a scaffold for forming a muscle substitute. According to this embodiment, an array of microfibers in the scaffold is arranged to mimic the configuration of muscle fibers in a muscle tissue. For example, in scaffolds for forming a skeletal muscle substitute, an array of microfibers is arranged to mimic the configuration of muscle fibers in skeletal muscle tissue. Similarly, in scaffolds for forming a cardiac muscle substitute, an array of microfibers is arranged to mimic the configuration of muscle fibers in cardiac muscle tissue.

The scaffold may comprise one or more layers of one or more parallel arrays of microfibers having a regular spacing. The scaffold may have between about 1 and about 20 layers (such as between 5 and 10 layers). The medical devices of this embodiment may further comprise cells cultured on the microfiber scaffold to form a skeletal muscle substitute. Typically, the cells cultured on scaffolds for forming skeletal muscle substitutes comprise skeletal muscle cells, for example myoblast cells. The cells cultured on scaffolds for forming cardiac muscle substitutes typically comprise cardial cells, such as cardiac muscle cells. The cells cultured on scaffolds for forming muscle substitutes may further comprise fibroblast cells.

In yet other embodiments, the implantable medical devices of the invention may comprise scaffolds for other tissues and organs in the body, including but not limited to, spinal cord, nerves, bone, cartilage, ligaments, tendons, heart valves, esophagus, cervix, bladder, skin, fascia, and other tissues. Such implantable medical devices comprise a scaffold comprising one or more arrays of controlled-diameter microfibers, wherein at least one of the arrays is arranged to mimic the configuration of one or more structural elements in the target tissue. In some embodiments, the implantable medical devices of the invention may further comprise cells cultured on the scaffold to form a target tissue substitute.

For example, in a medical device comprising a scaffold for an esophagus substitute, the scaffold may comprise at least two layers of at least two arrays of microfibers, wherein a first array of microfibers is arranged to mimic the configuration of the muscle fibers in the longitudinal muscle layer in the muscularis externa of the esophagus and a second array of microfibers is arranged to mimic the configuration of the muscle fibers in the circumferential muscle layer in the muscularis externa of the esophagus. The medical device comprising a scaffold for an esophagus substitute may further comprise cells cultured on the scaffold to form an esophagus substitute. Typically, the cells in this embodiment comprise muscle cells, for example myoblast cells.

In another illustrative embodiment, the medical device comprises a scaffold for forming a cartilage substitute. According to this embodiment, the scaffold may comprise one or more layers of one or more arrays of microfibers, wherein the arrays of microfibers are arranged to mimic the configuration of collagen fibers in fibrous cartilage tissue. The medical device comprising a scaffold for forming a cartilage substitute may further comprise cells cultured on the microfiber scaffold to form a cartilage substitute. Typically, the cells in this embodiment comprise chondrocytes. The cells in this embodiments may further comprise fibroblast cells.

In a further illustrative embodiment, the medical device comprises a scaffold for forming a mitral heart valve. According to this embodiment, the scaffold may comprise one or more layers of a plurality of arrays of microfibers, wherein the plurality of arrays of microfibers are arranged to mimic the configuration of collagen fibers in the mitral heart valve. The medical device comprising a scaffold for forming a mitral heart valve may further comprise cells, such as interstitial valvular cells, fibroblasts, smooth muscle cells, and endothelial cells, cultured on the microfiber scaffold to form an mitral heart valve substitute.

BRIEF DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein:

FIG. 3A shows a view of the microfiber 14 on a wound spool 12 being guided by a fiber guide 32 and applied in concentric layers to a frame of stainless steel rods 34 around a silicon elastomer tube 36 with a hub at each end 38 (only one hub is shown), and the extruder 40 for applying spacer fibers 42.

FIG. 10A shows a 3-dimensional array of microfibers 14, which mimic the orientation of muscle fibers in skeletal muscle tissue, and layers of muscle cells or fibers 100 in the skeletal muscle substitute.

FIG. 13A shows a view of the cartilage in the lumbar vertebrae.

FIG. 14A shows a schematic drawing of the mitral valve in systole from a perspective within the left atrium. Anterior and posterior cusps are coapted, which prevents backflow during contraction of the heart (Nuclear Medicine Mediabook (2000) Crump Institute).

DETAILED DESCRIPTION OF THE PREFERRED EMBODIMENT

Figure 1:
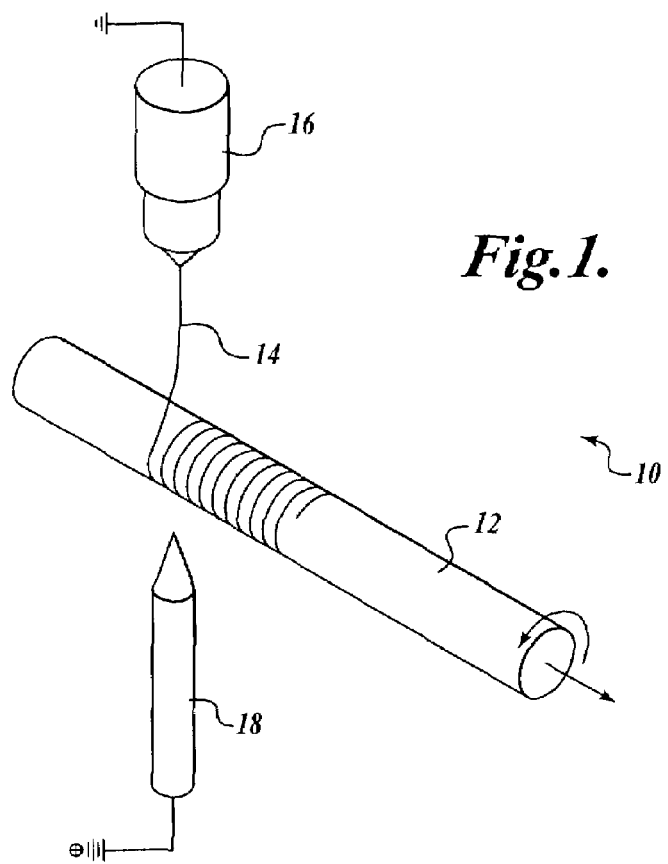
FIG. 1 shows an electrospinning system 10 to create spools 12 of microfibers 14 with precise diameters. When polymer solution in a polymer melt chamber 16 is subjected to an electric field, it travels towards the positive terminal 18 and is deposited on a rotating spool 12.

In one aspect, the invention provides methods of forming a target tissue substitute. The methods of the invention comprise the following steps: (a) providing a scaffold comprising one or more layers of one or more arrays of microfibers, wherein one or more of the arrays of microfibers is designed to mimic the configuration of one or more structural elements in a target tissue; and (b) culturing cells on the scaffold to produce a target tissue substitute.

The first step in the methods of the invention comprises providing a scaffold comprising at least one array of microfibers that is designed to mimic the configuration of one or more structural elements in a target tissue. As used herein, the term "structural element" refers to a component of a tissue that contributes to its characteristic architecture and mechanical properties. For example, the structural element may be natural fiber or a fibrous protein or a collection of fibrous proteins. The architecture of fibers and fibrous proteins in most tissues on the animal body has been well-characterized (see, e.g., Guyton (1981) *Textbook of Medical Physiology*, Saunders & Co., Philadelphia; Fawcett (1986) *A Textbook of Histology*, Saunders & Co., Philadelphia; Silver (1987) Biological Materials: *Structure, Mechanical Properties, and Modeling of Soft Tissues*, New York University Press, New York; Wainright et at. (1976) *Mechanical Design in Organisms*, Princeton University Press, Princeton). Exemplary structural elements that are mimicked in the methods of the invention include the elastin fibers in the medial layer of arterial blood vessels, muscle fibers in muscle tissues (such as skeletal muscle tissue and cardiac tissue) and esophagus, collagen fibers in heart valves, ligaments, tendons, skin, cervix, and fascia.

As used herein, the phrase "mimics the configuration of one or more structural element" or "designed to mimic the configuration of a structural element" or grammatical equivalents thereof refers to a design of a microarray, in which the microfibers emulate at least one aspect of the configuration of a structural element. Aspects of the configuration of a structural element include, for example, its orientation within the target tissue, its spacing, its dimensions, its curvature, its surface coating and surface charge, its composition, and its mechanical properties.

For example, the diameters of the microfibers may be chosen to mimic the diameters of a structural element of a target tissue. The dimensions of the microfibers are selected to permit the formation of a target tissue substitute that resembles the form and function of the target tissue. The microfibers may have a diameter between about 1 micrometer and about 20 micrometers (such as between about 1 and about 15 micrometers or between about 1 micrometers and about 6 micrometers). In some embodiments, the microfibers have a diameter between about 1 micrometer and about 15 micrometer, as described in EXAMPLES 1, 2, and 8. For example, fiber diameters for use in scaffold in blood vessel substitutes may be between about 1 micrometer and about 10 micrometers. This dimension has been shown to experience minimal encapsulation in soft tissues in vivo (Sanders et al. (2000) *J. Biomed. Mater. Res.* 52:231-7; Sanders et al. (2002) *J. Biomed. Mater. Res.* 62(2):222-7). Larger diameters (up to 40 micrometers) may be used, for example, in ligament substitutes.

Microfibers may be synthesized using a heat and draw method, as described in EXAMPLES 1, 3, and 8. Thus, polymer beads may be heated to its melting point until a fiber can be drawn around a tube mounted to the shaft of a motor-driven stirrer. Using this method, microfibers with diameters ranging from about 0.5 micrometers to several hundred micrometers may be created, depending on the melting temperature and the shaft rotation speed.

Alternatively, electrospinning may be used to create spools of less than 10 micrometer diameter microfibers. Electrospinning has been shown effective in other fields for generating long length (up to 1 km), small diameter, single fibers of consistent diameters (Reneker & Chun (1996) *Nanotechnol.* 7:216-23; Deitzel et al. (2001) *Polymer* 42:8163-70; Theron et al. (2001) *Nanotechnol.* 12:384-90). The concept of electrospinning is that when a polymer solution held by its surface tension at the end opening of a capillary tube is subjected to an electric field, charge is induced at the liquid surface. Mutual charge repulsion causes a force directed opposite to the surface tension. When the electric field intensity is sufficiently strong, forces on the surface of the solution at the tip of the capillary overcome the surface tension, the surface elongates, and makes a fine jet in the direction of the applied field (perpendicular to the liquid surface). As the jet travels towards the positive terminal of the applied voltage, usually connected to a plate, screen, or rotating mandrel positioned at least a few centimeters beneath the nozzle, it solidifies, forming fine fibers that collect on the plate, screen, or mandrel. Microfibers as small as 50 nm in diameter have been fabricated using the electrospinning technique (Doshi & Reneker (1995) *J. Electrostatics* 35:151-60).

FIG. 1 shows an electrospinning system 10 to create spools 12 of microfibers 14 with precise diameters. When polymer solution in a polymer melt chamber 16 is subjected to an electric field, a fine jet of polymer travels towards the positive terminal 18 and is deposited on rotating spool 12. The rotating spool 12 is also translated, using the translational stage on the electrospinning system, to ensure no fiber overlapping occurs.

The mechanical properties of the polymer used to make the microfibers are also selected to permit the formation of a tissue substitute that resembles the form and function of the target tissue. Thus, a polymer may be chosen that has material properties similar to those of the structural elements in a target tissue. A variety of synthetic polymers may be used in the microfiber scaffolds of the invention. Virtually any synthetic polymer or mixtures of synthetic polymers may be used in the microfiber scaffold. Representative examples of synthetic polymers useful for making the fibers in the scaffolds include, but are not limited to: silicones, carbonized polyurethane, nylon, polypropylene, polyethylene, polyurethane, polyester, polytetrafluoroethylene (PTFE), poly(lactic acid), poly(glycolic acid), polystyrene, polycarbonate, polyethylene glycol (PEG), fluoropolymers, poly(galactic acid), polyethylene terephthalate (PET), poly(dioxanone), poly(trimethylene carbonate)copolymers, poly (e-caprolactone) homopolymers and copolymers, polyanhydrides, polyorthoesters, and copolymers of any of any of the foregoing. Representative examples of natural polymers useful for making the fibers include proteins (such as collagen elastin, chitosan), carbohydrates and glycosaminoglycans.

In some embodiments, a non-degradable polymer may be used to provide a permanent matrix. Non-degradable polymer microfibers were used in the blood vessel substitutes described in EXAMPLES 1, 2, and 8 because the purpose was only to evaluate the microfiber array concept, not the scaffold material. Use of degradable materials would have confounded interpretation of the data.

In some embodiments, the microfibers are made of a biodegradable material that gradually transfers load from the scaffold to the target tissue substitute, as described in EXAMPLE 3. Thus, polymer stiffness is designed to decrease over time so that load is effectively transferred to the growing tissue, as described in EXAMPLE 6. Use of degradable materials also avoid in vivo fibrous encapsulation in the long term. Presently preferred materials for use in the microfiber scaffold of the invention exhibit the following properties: (a) they promote cell adhesion and spreading upon cell seeding, facilitating the production and assembly of extracellular matrix proteins; (b) they produce degradation byproducts that are biocompatible in vivo; (c) they exhibit an initial modulus comparable to or slightly greater than that of one or more structural elements (such as a fibrous protein) in the target tissue, and that reduces over time to effectively transfer load to the tissue substitute as is matures, and (d) the material is easily manufacturable into different architectures. As used herein, the term "Young's modulus" or "modulus" refers to a numerical constant that describes the elastic properties of a solid undergoing tension or compression in only one direction. Young's modulus is the slope of the linear region of the stress-strain diagram and is described, for example, in Timoshenko & Gere (1972) *Mechanics of Materials.* New York, D. Van Nostrand Company, which publication is incorporated herein by reference.

Exemplary biodegradable materials for use in the microfibers of the invention include, for example, poly-L-lactic acid/polycaprolactone co-polymers, a poly-caprolactone/poly-caprolactone-co-glycolide/poly-hydroxybutyrate-co-hydroxyvalerate/urethane co-polymers, degradable polyurethane, and polyglycolic acid.

The biocompatibility of degradable polymer materials may be assessed in vivo, as described in EXAMPLE 5. The substrate modulus and degradation rates of polymers may be optimized by adjusting the polymer compositions, as described in EXAMPLE 6.

According to the invention, the arrays of microfibers in the scaffolds used in the methods of the invention may comprise microfibers having a diameter, spacing, orientation, and mechanical properties comparable to one or more fibers or fibrous proteins or collection of fibrous proteins in the target tissue. The microfibers in the scaffolds of the invention are typically oriented in a non-random manner, such as helically or concentrically, or aligned in parallel, or oriented at a defined angle with respect to adjacent fibers. There may be more than one layer of a structural element in a target tissue. Thus, the scaffold may comprise more than one layer of one or more microfiber arrays, and the number and spacing of the layers in the scaffold may be designed to reflect the number and spacing of the corresponding layers in the target tissue.

The microfibers in an array typically have a regular spacing. The spacing between adjacent microfibers in an array may be between about 10 micrometers and 100 micrometers (such as between about 30 micrometers and about 70 micrometers or about 40 micrometers and about 60 micrometers). The optimal spacing between adjacent fibers in an array may be determined empirically, as described in EXAMPLES 1 and 8. Microfiber spacing is typically designed to provide the correct stimulus for the cells used to make the tissue substitute. For some tissue substitutes, for example blood vessel substitutes as described in EXAMPLE 1, an optimal fiber spacing is selected to permit the formation of continuous and precisely aligned cell layers of uniform thickness, as is observed in normal tissue development. Excessive spacing may results in gaps or holes where cells do not grow into confluency. Thus, the overall architecture of the scaffold may affect the organization of the tissue substitute. For example, the use a mesh-like scaffold may result in a disorganized tissue structure with respect to the orientation of cells, as well as the protein synthesized by the cells (for example, collagen), as shown in EXAMPLE 1. This disorganized pattern generally bears no resemblance to the natural tissue. By contrast, the use of a scaffold comprising arrays of microfibers that are designed to mimic the configuration of one or more structural elements in the target tissue permits the growth and organization of cells, as well as the synthesis and patterning of matrix proteins, such as collagen and elastin, to produce a tissue substitute that closely resembles the natural target tissue.

Figure 2A:
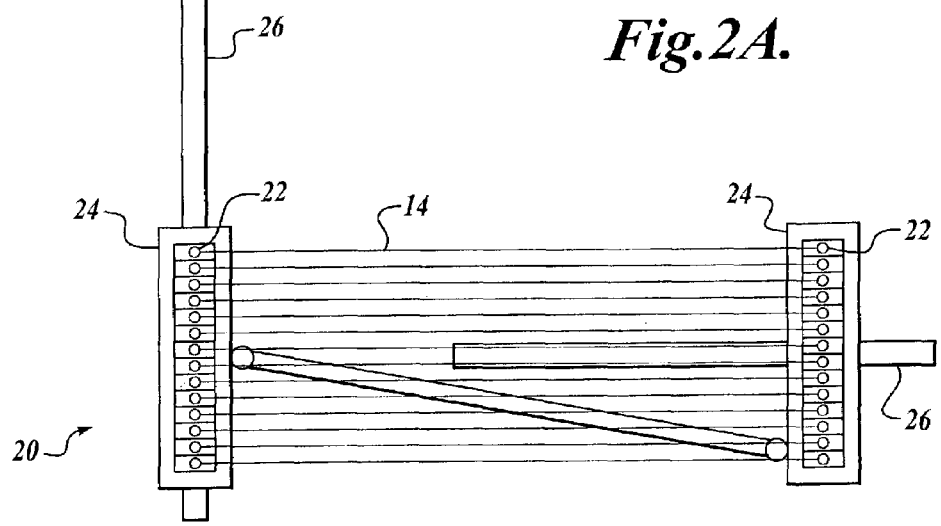
FIGS. 2A and B show two schematic drawings of a system 20 for aligning microfibers, as described in EXAMPLE 1. Microfibers 14 are strung between the teeth 22 of two lice combs 24, mounted on slide rails 26 (FIG. 2A). To decrease fiber spacing, the combs 24 are moved on the slide rails such that the fibers stay parallel to each other (FIG. 2B).
Figure 2B:
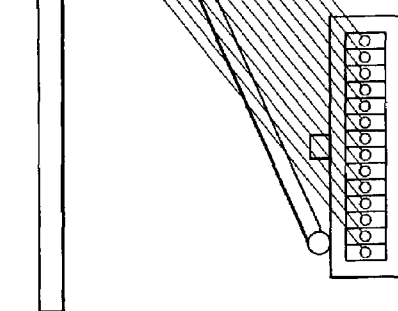

The spacing of adjacent microfibers in a linear, parallel microfiber array may be adjusted, for example, by using the apparatus shown in FIG. 2. Microfibers 14 are strung between the teeth 22 of two lice combs 24 mounted on slide rails 26 (FIG. 2A). To decrease fiber spacing, the combs 24 are moved on the slide rails such that the fibers stay parallel to each other (FIG. 2B). The use of any other apparatus to create a parallel, linear array of regularly spaced microfibers is also within the scope of the invention.

Figure 3A:
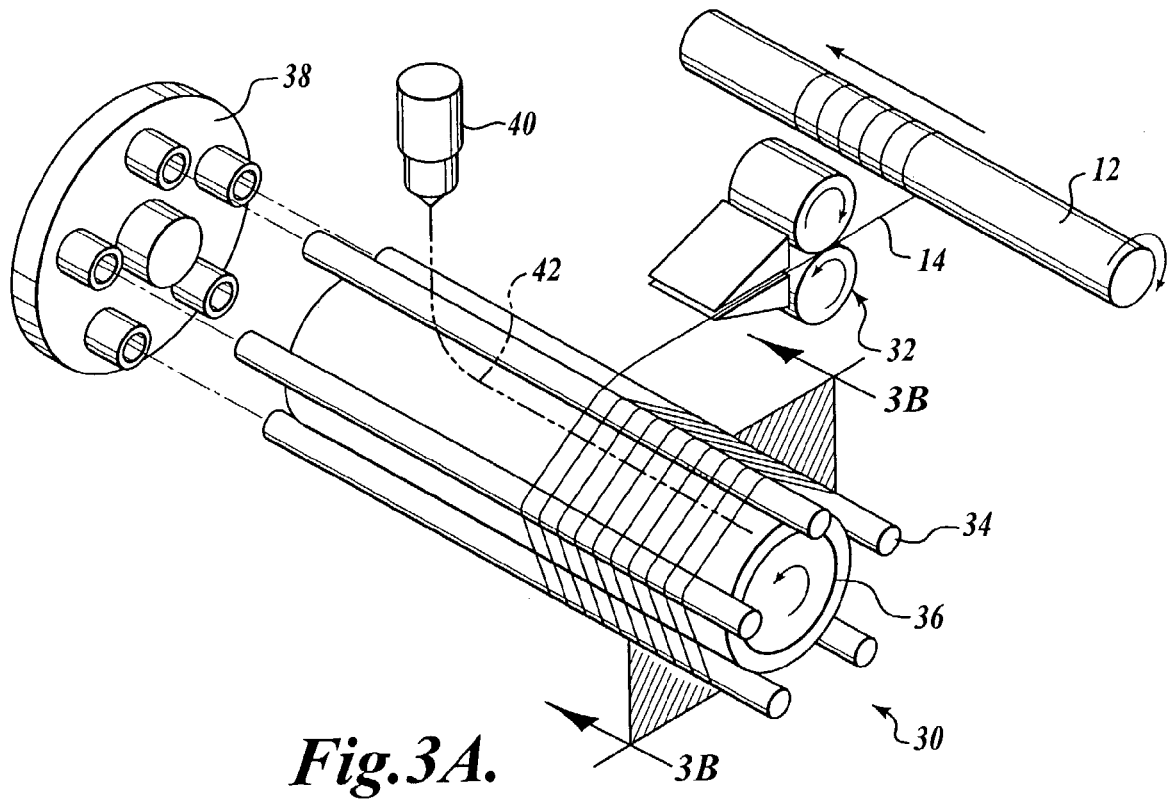
FIGS. 3A and B shows an embodiment of a medical device of the invention 30 and a system for assembling concentric layers of microfibers to form a tubular scaffold.
Figure 3B:
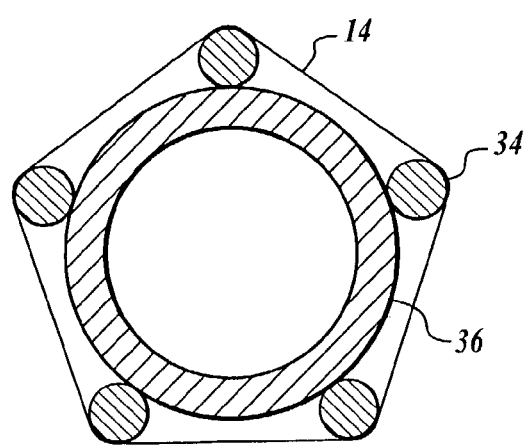
FIG. 3B shows a cross-sectional view of the fiber 14 wrapped around the frame of stainless steel rods 34 and elastomeric tube 36.

A tubular array of regularly spaced microfibers may be assembled using a system as shown in FIG. 3, and as further described below. Briefly, a microfiber 14 on a wound spool 12 may be guided by a translating fiber guide 32 and applied in concentric layers to a frame of stainless steel rods 34, whose central axis is rotated. The use of any other apparatus to create a tubular array regularly spaced microfibers is also within the scope of the invention.

The arrays of microfibers in a scaffold may be arranged in one or more layers. The spacing between layers of microfiber arrays in scaffolds with multiple layers of arrays is designed to permit the formation of cell layers that reflect the alignment and thickness that is observed in the development of the target tissue. The layers of arrays of microfibers in the scaffold are typically regularly spaced. The spacing between the layers may be between about 10 micrometers and 200 micrometers (such as between about 60 micrometers and about 160 micrometers or between about 80 micrometers and about 120 micrometers). The optimal spacing between the layers in the scaffold for the methods of the invention may be determined empirically, as described in EXAMPLE 1.

Figure 4:
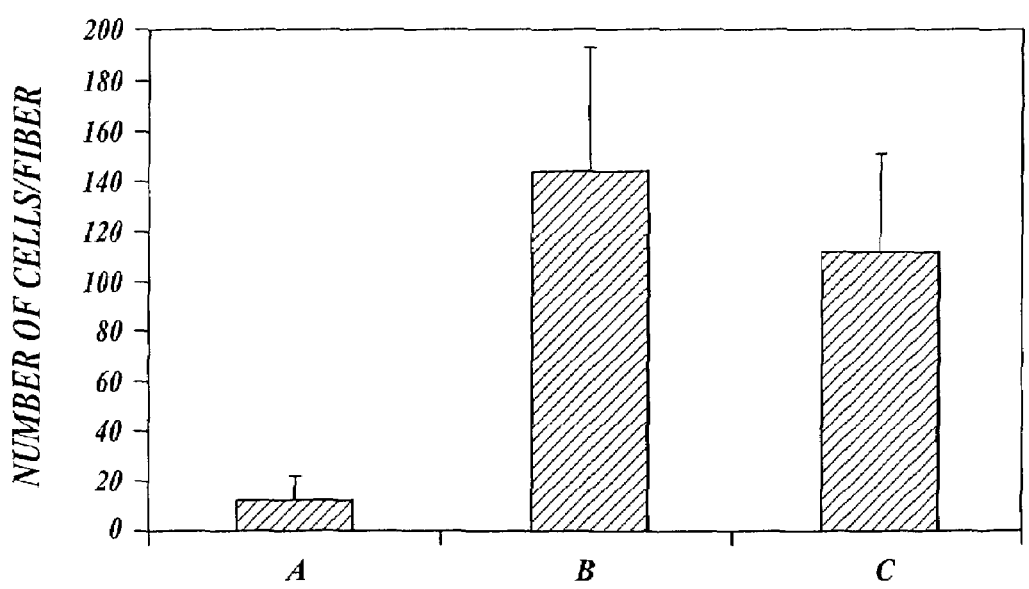
FIG. 4 shows a chart documenting the attachment of cells 30 minutes after seeding to uncoated microfibers (A), fibronectin-coated fibers (B), and laminin-coated fibers (C), as described in EXAMPLE 1.

The microfiber scaffold may further comprise a coating comprising a cell adhesion-enhancing agent to promote cell adhesion and spreading, as shown in FIG. 4. Illustrative cell adhesion-enhancing agents include, for example, elastin, laminin, and collagen. The scaffold is typically coated by incubating it in a solution comprising a cell adhesion-enhancing agent under conditions effective to promote the coating of the scaffold. Exemplary methods of coating microfiber scaffolds are described in EXAMPLES 1, 4, and 8.

In the second step of the methods, cells are cultured on the microfiber scaffold to produce a target tissue substitute. The structural characteristics microfiber scaffold direct the adhesion, migration, alignment, differentiation, and behavior of the cells to produce a target tissue substitute with a substantially similar architecture and function as the target tissue. A target tissue substitute with a substantially similar architecture has a morphologically similar arrangement of cells and extracellular matrix to that found in the target tissue. A target tissue substitute with a substantially similar function is able to replace all or most of the function of the target tissue. Thus, appropriate cell types to culture on the scaffold are the cell types, or a subset of the cell types, that are present during the development of the target tissue, as described in illustrative embodiments below and, for example, in EXAMPLES 1, 7 and 8.

Figure 5:
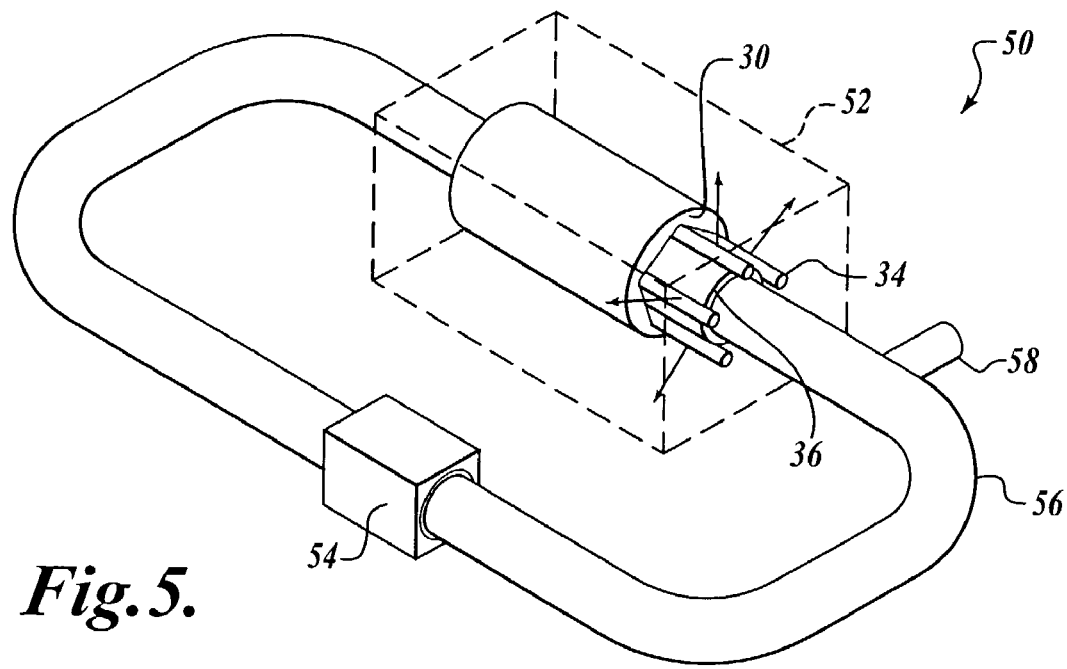
FIG. 5 shows an embodiment of a tubular scaffold for a tissue substitute of the invention 30 in a system for dynamic mechanical conditioning 50. The tissue substitute 30 is positioned into a media-filled compliance chamber 52 via insert connections in stainless steel tubes 34. A pulsatile flow pump 54 is connected to the silicon elastomer tube 36 via a stainless steel tube 56. Pressure of the fluid in the silicon tube 36 is measured using a pressure gauge 58.

In some embodiments, the cells are cultured on the microfiber scaffold in the presence of dynamic mechanical conditioning. Dynamic mechanical conditioning simulates the working environment of the target tissue. A system of dynamic mechanical conditioning applies cyclic strains to the tissue substitute in culture. A system for dynamic mechanical conditioning is shown in FIG. 5, and is further described below. Briefly, a silicon elastomer tube 36 may be inserted into a tubular scaffold. The tubular scaffold and cells adhering to the scaffold may be positioned into a media-filled compliance chamber 52 and subjected to pulsatile flow from pump 54 connected to the silicon elastomer tube via a stainless steel tube 56. Pressure of the fluid in the silicon tube 36 is measured using a pressure gauge 58.

In one embodiment, the invention provides methods for forming blood vessel substitutes. In this embodiment, the target tissue may be an arterial blood vessel. An arterial blood vessel comprises three layers, an inner layer (intima), a medial layer, and an outer layer (adventitia). Most of the mechanical support is provided by the medial layer, shown in FIG. 6. The structure of the medial layer 60 is very specific and a key to its function (Clark & Glagow (1985) *Arteriosclerosis* 5(1):19-34; Clark & Glagov (1979) *Lab. Invest.* 40(5):587-602). Elastic lamellar helices 62 (at 1 to 25° with the longitudinal axis) (fiber diameter 1-10 micrometers) are arranged in 7-23 concentric layers around the intima (Clark & Glagow (1985) *Arteriosclerosis* 5(1):19-34; Canham et al. (1997) *Cardiovasc. Res.* 34(3):557-67). Smooth muscle cells (SMCs) 64 with their surrounding fine collagen networks fill the spaces between elastin layers. Some wavy collagen fibers align with the elastin. Lamellar layers are spaced at least 50 micrometers apart in the radial direction. In the narrow spaces between adjacent winds of elastin fibers, cell-cell attachments and cell alignment ensure effective load support there. This architecture provides radial and tangential strength as well as longitudinal elasticity to the vessel structure.

According to this embodiment, the methods of forming blood vessel substitutes comprise (a) providing a tubular scaffold comprising one or more layers of an array of microfibers, wherein the array of microfibers is designed to mimic the array of elastin in the medial layer of an arterial blood vessel; and (b) culturing cells on the scaffold to produce a blood vessel substitute.

The first step in the formation of blood vessel substitutes comprises providing a microfiber scaffold in which the array of microfibers is designed to mimic the arrangement of elastin in the medial layer of an arterial blood vessel, as described in EXAMPLES 1 and 2. The scaffold is typically tubular and comprises one or more layers of a helical array of regularly-spaced microfibers. The diameter of the microfibers may be between about 1 micrometer and about 20 micrometers (such as between about 1 micrometers and about 15 micrometers or between about 1 micrometers and about 6 micrometers. Typically, the diameter of the microfibers is between about 1 micrometer and about 10 micrometer. This microfiber diameter is consistent with the elastic lamellae sizes in natural arteries (Clark & Glagov (1985) *Arteriosclerosis* 5(1):19-34) and is a dimension that has been shown to experience minimal encapsulation in soft tissues in vivo (Sanders et al. (2000) *J. Biomed. Mater. Res.* 52:231-7; Sanders et al. (2002) *J. Biomed. Mater. Res.* 62(2):222-7).

The microfibers may be created using any method known in the art. For example, the microfibers may be made using a heat and draw method, as described in EXAMPLES 1 and 3. Alternatively, electrospinning may be used to create spools of less than 10 micrometer diameter microfibers, such as the electrospinning system shown in FIG. 1. Fibers 14 are drawn onto a rotating spool 12 that is also translated, using the translational stage on the electrospinning system 10, to ensure no fiber overlapping occurs.

An exemplary system that provides quick and reliable assembly of concentric layers of microfibers arrays to form a tubular scaffold for making blood vessel substitutes is shown in FIG. 3A. The system consists of a frame structure made up of five 0.36-mm-OD stainless-steel rods 34 (Hypodermic, Small Parts, Miami Lakes, Fla.) positioned equidistant from a central axis. A microfiber 14 is wrapped around this frame to generate a lamellar layer. To ensure the 5 rods remain stable during fiber-array construction, hubs 34 hold the rods at the ends. Also, a 1.19-mm-OD (0.64-mm-ID) silicon elastomer tube 36 (60-011-03, Helix Medical Inc., Carpinteria, Calif.) is positioned within the frame and filled with fluid to make it sufficiently stiff to prevent bending of the rods during fiber wrapping.

Five longitudinal members are sufficient to generate a tubular vessel substitute. However, additional members may be added if a more rounded cross-section is required, or if fiber strain at the vertices is excessive during fabrication or during dynamic mechanical conditioning. The hub axis, uniaxial with the frame central axis, is rotated using a servomotor (Compumotor SM232, Rohnert Park, Calif.).

A torque sensor is positioned between the motor and the hub axis to provide feedback to a PC-based proportional-integral-derivative (PID) controller that will adjust motor speed based on the applied torque. This control ensures that microfibers are not overstressed while they are being wound onto the frame. The other end of the system has a hub supported by a low-friction radial bearing.

To make a single uniform-diameter layer, microfiber from a spool 12 is drawn through a fiber guide 32 onto the frame with stainless steel rods 34 in a helical configuration while the frame central axis is rotated. The use of a collection spool, as opposed to electrospinning directly onto the 5 stainless steel rods, prevents fibers from aligning with the rods in the electric field, distorting the winding. The fiber guide 32 is translated using a linear slide rail under computer control. A 10° fiber angle with the cross-section may be used, consistent with mid-range measurements of fiber angles in internal mammary arteries (Canham et al. (1997) *Cardiovasc. Res.* 34(3):557-67), the most successful graft for coronary bypass. This natural feature provides longitudinal elasticity and strength to the artery (Canham et al. (1997) *Cardiovasc. Res.* 34(3):557-67).

An optical-based position sensor and feedback control may also be used to provide sufficient fiber alignment to ensure an acceptable resolution in spacing. Because overstraining the microfiber is a concern, the spool 12 is put on a controlled motor axis that is also instrumented with a torque sensor to provide controller feedback, in addition to controlling the central axis speed based on the applied torque. An idler may be used to further limit fiber tension. The microfiber 14 may be slightly loaded at a consistent tension during winding using this configuration, so that it does not slip on the frame once assembled. The stainless steel longitudinal segments 34 may be coated with a non-fouling surface (poly(ethylene glycol), PEG) applied with plasma-coating methods) so that cells do not attach to them in culture and grow the frame into the vessel substitute. Because plasma-coating methods can put down a very smooth even surface, plasma coating will also serve to lubricate the fiber on the tubes if overstressing during dynamic mechanical conditioning proves to be a problem.

Once the first layer of microfiber 14 is created, 60-80 micrometer diameter biodegradable spacer fibers 42 are positioned longitudinally on the external microfiber surface, parallel with the longitudinal stainless steel rods 34. These spacer fibers 42 are intended to serve as spacers between adjacent layers during assembly, and during in vitro culturing and mechanical straining. A spacing between layers of least a 60 micrometers is typically used to prevent interaction between fiber layers, as described in EXAMPLE 1. These longitudinal fibers have a higher modulus and lower degradation rate than the concentrically wound fibers 14 to provide adequate longitudinal stability during culturing. These features can be achieved by adjusting the polymer compositions, as described in EXAMPLE 6. To align the spacer fibers to be radially adjacent to the stainless-steel rods, an extruder 40 is used. The extruder may either be translated, or left stationary while translating the scaffold during this phase, for example, by using a linear stage. The longitudinal fibers 42 may be bonded to the wound microfiber layer to prevent slippage when another layer is added. Thus, the longitudinal fibers may be coated with PLA or PLGA before application (Ali et al. (1994) *Biomater.* 15(10):779-85). Alternatively, a controlled heating element may be added to the extruder 40. It is possible to achieve very fine control of polymer temperature using this method. The fibers are deformable but not molten as they emerge from the nozzle, thus they stick to the wound-fiber layer but maintain an approximately circular shape. Once these longitudinal fibers are assembled, another layer of microfiber 14 is added, increasing the scaffold diameter. This process is repeated until the desired number of layers of microfibers 14 are assembled, for example between 7-23 layers, consistent with natural artery (Clark & Glagow (1985) *Arteriosclerosis* 5(1):19-34).

Any other system for assembling scaffolds for blood vessel substitutes is also within scope of the invention. For example, tubular scaffolds for blood vessel substitutes may also be assembled by wrapping concentric layers of microfibers around a mandrel (a thin candy cane), stabilized with longitudinal fibers and end rings, as described in EXAMPLE 2.

In some embodiments, the spacing between the fibers is between about 10 micrometers and about 100 micrometers, such as between about 30 micrometers and about 70 micrometers or between about 40 micrometers and about 60 micrometers, as described in EXAMPLES 1 and 2. Undesired fiber clustering occurred at very small spacings (10-20 micrometers) because cell traction forces were sufficiently strong to group fibers into bundles at these short distances. At very large spacings (80-100 micrometers) the distances between adjacent fibers were too large for the cells to bridge the gaps. Layers around individual 10-micrometer fibers stabilized by 21 days to 20-40 micrometers, thus cells cannot migrate the additional distance between cell layer edges (20 to 60 micrometers) to establish contact with the adjacent fiber layer. The intermediate spacing of 40-60 micrometers is an effective compromise between these two opposing factors, as shown in EXAMPLE 1.

In some embodiments, the scaffold for a blood vessel substitute comprises between 2 and 25 layers (such as between 3 and 10 layers), consistent with the 7-23 layers in the natural arteries, (Clark & Glagow (1985) *Arteriosclerosis* 5(1):19-34). The spacing between layers in the scaffold may be between about 10 micrometers to about 200 micrometers, such as between about 60 micrometers and 160 micrometers or between about 80 micrometers and about 120 micrometers. In some embodiments, the layers of arrays have a spacing of between about 20 micrometers and 80 micrometers, as described in EXAMPLES 1 and 2.

Typically, the scaffold is coated with an adhesion-enhancing agent before culturing cells on the scaffold to promote the adhesion and spreading of cells, as shown in FIG. 4. Exemplary cell adhesion-enhancing agents include, for example, fibronectin, laminin, and collagen. Effective cell-fiber coupling is important to the generation of continuous tissue between fibers, because coating the fibers with adhesive proteins is required for cell layers to be created between adjacent microfibers. Greater cell attachment to fibronectin-coated fibers was observed than to fibers coated with laminin (see FIG. 3). This result consistent with results obtained with endothelial cells (Balcells & Edelman (2002) *J. Cell. Physiol.* 191(2):155-61). However, the lack of a difference in cell layer thickness observed after culturing the scaffolds for 3 weeks suggests both laminin and fibronection are appropriate adhesion-enhancing agents for use on the scaffolds of the invention.

In the second step in the formation of blood vessel substitutes of the invention, cells are cultured on the microfiber scaffold to form a substitute blood vessel. The scaffold directs the adhesion and behavior of cells to produce a blood vessel substitute having a substantially similar architecture and function as the natural blood vessel. Typically, the cells comprise smooth muscle cells (SMCs). The SMCs align between adjacent segments of microfiber, i.e., adjacent winds in each helix, to form strong cell layers between them, as shown in EXAMPLES 1 and 2. Typically, the distance between adjacent segments is short, to reduce the distance for cell migration after seeding to achieve a continuous cell layer between adjacent fiber segments and the culture time necessary to form the medial layer of a small diameter vessel substitute.

In some embodiments, smooth muscles cells are cultured on the microfiber scaffold in the presence of dynamic mechanical conditioning. In these embodiments, the scaffold including the stainless steel rods 34 and silicon tube 36 may be disconnected from the motor drive, put into a dynamic mechanical conditioning system, seeded with cells, and cultured while applying cyclic strains.

An examplary system for dynamic mechanical conditioning is described in FIG. 5. The system 50 is based on previously described dynamic mechanical stimulation systems (Niklason et al. (1999) *Science* 284(5413):489-93; Conklin et al. (2000) *Med. Eng. Phys.* 22(6):441-9; Peng et al. (2000)

*Am. J. Physiol. Cell Physiol.* 279(3):C797-805; Seliktar et al. (2000) *Ann. Biomed. Eng.* 28(4):351-62).

The scaffold for forming a blood vessel substitute 30 is positioned into the dynamic mechanical conditioning system via insert connections in the stainless-steel tubes 34. Each connection is hinged at two points with a slide to compensate for translation to permit only radial displacement of each tube 34 during straining. The hinges and other surfaces are plasma-coated with polyethylene glycol so as to prevent clogging while in media. Mechanical guides may also be used instead of the hinges to prevent clogging. A pulsatile flow pump 54 (Harvard Pulsatile Blood Pump, Harvard Apparatus Inc., Holliston Mass.) is connected to the silicon elastomer tube 36 via a stainless steel tube 56 of sufficient length to ensure laminar flow. A compliance chamber 52 may be added to dampen high-frequency oscillations.

Pressure of the fluid in the silicon tube 36 is monitored with a pressure transducer 58 to provide feedback to a PC-based PID controller. The use of an inflatable tube to deliver strain to the blood vessel substitute is similar to previous designs (Niklason et al. (1999) *Science* 284(5413):489-93; Conklin et al. (2000) *Med. Eng. Phys.* 22(6):441-9; Peng et al. (2000) *Am. J. Physiol. Cell Physiol.* 279(3):C797-805; Seliktar et al. (2000) *Ann. Biomed. Eng.* 28(4):351-62), however, in the design shown in FIG. 5 the blood vessel substitute is not in direct contact with the distensible tubing, and the radial strain is measured. Strain is assessed using a real-time video edge detection system, which is a CCD digital video camera (Model 1310M, DVC, Austin, Tex.) and image capture board (EPIX, Inc.; Buffalo Grove, Ill.). Positions of markers on the stainless steel rods are tracked over time and used to compute vessel radial and tangential strains. Vertical segments from the stainless steel rods may be extended out of the media bath to serve as markers.

Strains up to 30%, consistent with maximum in vivo levels for arteries (Pelc (1995) *JMRI* 5:339-45), may be achieved by inflating the silicon tube 36, without it (burst pressure=36,000 mm Hg) or expanding it excessively between the stainless steel rods 34 to contact the fibers. However, strains of ≦10% are sufficient based on previous results (Kim et al. (1999) *Nat. Biotechnol.* 17(10):979-83; Niklason et al. (1999) *Science* 284(5413):489-93; Seliktar et al. (2000) *Ann. Biomed. Eng.* 28(4):351-62). All candidate microfiber materials (see EXAMPLE 3) showed recoverable strains under tensile loading up to 30%, making fatigue or failure of the wound fibers unlikely. If stress concentrations in the fiber contacting the stainless-steel rods occur, then more stainless-steel members 34 may be added. A loading frequency of 1 Hz may be used. After sufficient tissue is generated to make the construct non-leaky, the silicone elastomer tube 36 is removed, and the vessel substitute is attached directly to the flow system via Dacron sleeve connections to apply cyclic fluid flow through the blood vessel substitute.

For initial testing, the system may be placed in a commercial incubator maintained at 37.5° C. and 5% [$CO_2$]. To strain a number of vessel substitutes simultaneously, additional test segments and pumps are added to the system. A commercial environmental control system (Gasmix 20, Wave Biotech, Bridgewater, N.J.) may be used instead of the incubator, pumping a 5% $CO_2$/95% air mixture into the chamber. Heaters and controllers (SH-27B and TC-324B, Warner Instrument Corp., Hamden, Conn.) may be used to control media temperature to 37.5° C. Media exchange every 2-3 days is facilitated with a peristaltic pump (Model 1203, Harvard Apparatus, Inc., Holliston, Mass.). To evaluate performance of the system for dynamic mechanical conditioning, comparisons are made between the control input pressure profiles and those actually measured. Performance of the strain measurement instrument is assessed by evaluating elastomeric tubes of known modulus.

Figure 7:
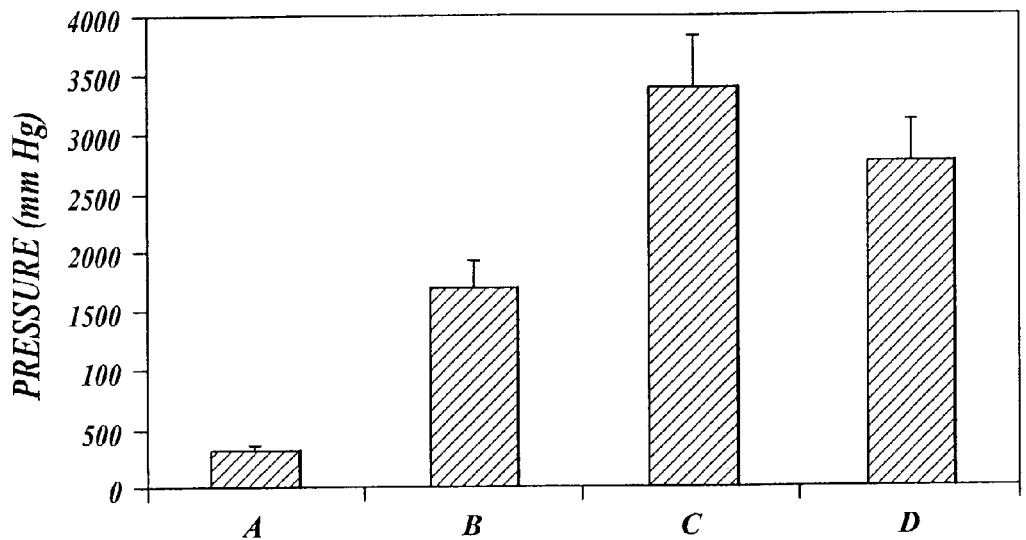
FIG. 7 shows a chart documenting the burst pressures observed using a linear microfiber array after 7 days (A), a linear microfiber array after 14 days (B), a tubular array after 80 days (C), and rat small intestine (D), as described in EXAMPLES 1 and 2.

A two-layered linear tissue substitute formed using the methods described herein, exhibited a high magnitude of strength compared with rat intestinal tissue in a culture time interval of 14 days, as described in EXAMPLE 1 and shown in FIG. 7. This indicates that cell-to-cell attachments and cell-to-extracellular matrix attachments obtained using the methods of the invention to make tissue substitutes are strong.

Figure 8:
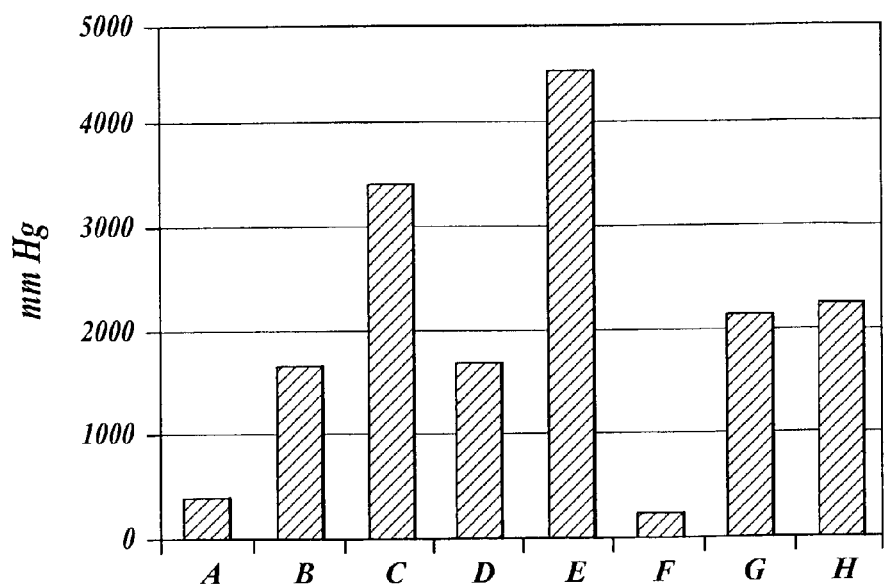
FIG. 8 shows a chart documenting the burst pressures observed using a vessel substitute of the invention after 7 days (A), the vessel substitute of the invention after 14 days (B), the vessel substitute of the invention after 80 days (C), a saphenous vein (D), a small diameter artery (E), a collagen gel construct with dynamic mechanical conditioning after 10 days (F) (Nerem & Seliktar (2001) *Annu. Rev. Biomed. Eng.* 3:225-43), a polyglycolic acid matrix cultured under pulsatile flow conditions after 56 days (G) (Niklason et al. (1999) *Science* 284(5413):489-93), and a tubular construct of SMCs and dermal fibroblasts after 90 days (H) (L'Heureux et al. (1998) *FASEB J.* 12(1):47-56), as described in EXAMPLE 2.

Using the methods described herein, blood vessel substitutes having three layers of microfibers have been prepared that have a burst pressure of more than 1500 mm Hg after 2 weeks of culture in the absence of mechanical conditioning, as shown in FIGS. 7C and 8. In some embodiments, the burst pressure of the blood vessel substitutes produced according to the methods of the invention is more than 3000 mm Hg, as shown in FIGS. 7C and 8. In some embodiments, the methods provide blood vessel substitutes that are ready for implantation after 2 weeks of culture or less, as described in EXAMPLE 2. In some embodiments, the use of dynamic mechanical conditioning in the methods of the invention reduces fabrication time to less than 2 weeks and enhances the mechanical quality of the blood vessel substitute.

The blood vessel substitutes of the invention may further comprise other cell types, such as endothelial cells and/or fibroblasts, as described in EXAMPLE 7. Endothelial cells may be suspended in growth medium and allowed to attach to the inner circumference of the blood vessel substitute to form an intima. Fibroblasts and collagen may also be added to the outer circumference of the blood vessel substitute to form an adventita.

Figure 9:
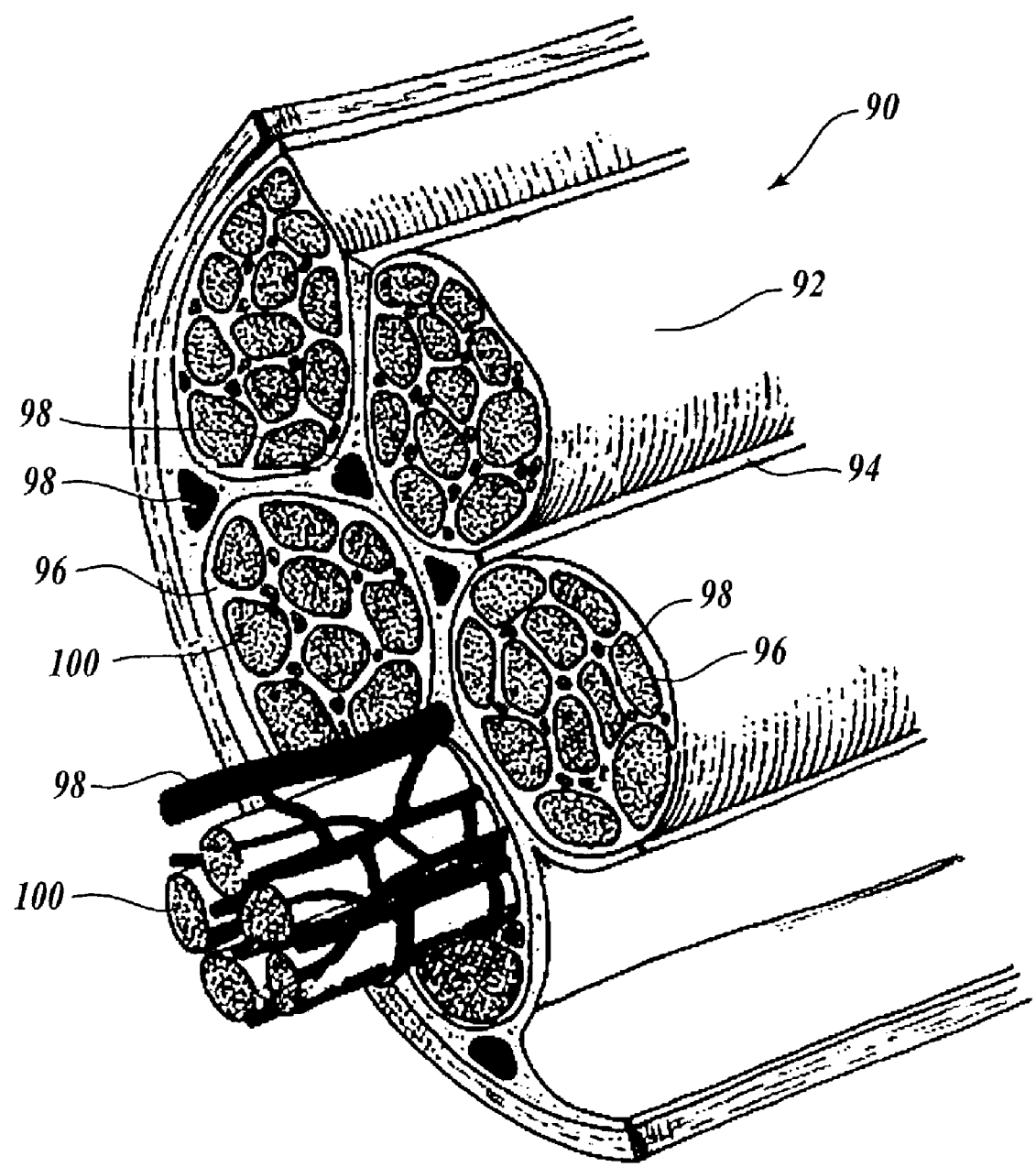
FIG. 9 shows the arrangement of fibrous protein in skeletal muscle tissue 90. Skeletal muscle consists of parallel fibers 100 and blood vessels 98, organized in fascicles 92, which are surrounded by perimysium 94. A sheet of connective tissue called endomysium 96 surrounds each fiber.

In another embodiment of the invention, the target tissue is muscle tissue. The arrangement of fibrous protein in skeletal muscle tissue is shown in FIG. 9. Skeletal muscle consists of parallel muscle fibers 100 and blood vessels 98 organized in fascicles 92, which are surrounded by perimysium 94. A sheet of connective tissue called endomysium 96 surrounds each fiber.

According to the invention, the methods of forming muscle substitutes comprise (a) providing a linear scaffold comprising one or more layers of an array of microfibers, wherein the array of microfibers is designed to mimic the configuration of muscle fibers in muscle tissue; and (b) culturing cells on the scaffold to form a muscle substitute. For example, a scaffold for forming a skeletal muscle substitute comprising one or more layers of an array of microfibers, wherein the array of microfibers is designed to mimic the configuration of muscle fibers in skeletal muscle tissue. A scaffold for forming a cardiac muscle substitute comprising one or more layers of an array of microfibers, wherein the array of microfibers is designed to mimic the configuration of muscle fibers in cardiac muscle tissue.

The first step of these embodiments of the methods of the invention comprises providing a scaffold comprising an array of microfibers that mimics the configuration of muscle fibers in skeletal muscle. Scaffolds for muscle substitutes must meet several tissue-specific demands. The muscle cells in the muscle substitute have to be stimulated to orient themselves parallel to each other in order to ensure directed force production. The percentage of scaffold material within the muscle substitute should be as low as possible to obtain a high ratio of contractile to restrictive components. Sufficient strength, a defined size and shape, and the ability to surgically attach the muscle substitutes are required for most clinical applications, such as the repair of congenital diaphragmatic hernia. In addition, general bioengineering requirements, including biocompatibility and the ability to vascularize, are important.

The scaffold for forming a muscle substitute may be linear and comprise one or more layers of a parallel array of microfibers having a regular spacing. The diameter of the microfibers may be between about 1 micrometer and about 20 micrometers (such as between about 1 micrometers and about 15 micrometers or between about 1 micrometers and about 6 micrometers.

Microfibers may be made, for example, by using a heat-draw method, as described in EXAMPLES 3 and 8, or by electrospinning, as shown in FIG. 1. Other methods of making microfibers for use in the methods of forming a skeletal muscle substitute are also within the scope of the invention.

An exemplary system for making linear arrays for use in forming skeletal muscle substitutes is described in EXAMPLE 8. For example, the microfibers may be assembled into 2-dimensional arrays by using the system described in FIG. 2. Thus, microfibers 14 may be strung between teeth 22 of two opposite-facing lice combs 24. By adjusting the positions of the combs 24 on slide rails 26, the spacings between adjacent microfibers may controlled. The microfibers may be sandwiched between the sticky sides of two mylar frames coated on one side with a 25-micrometer thick adhesive layer to keep the fibers stationary. Larger 3-dimensional scaffolds may be created by arranging fibers in several layers or by stacking of cellular sheets. Any other system for assembling scaffolds for blood vessel substitutes is also within scope of the invention.

In some embodiments, the spacing between the fibers is between about 10 micrometers and about 100 micrometers, such as between about 30 micrometers and about 70 micrometers or between about 40 micrometers and about 60 micrometers. In some embodiments, the spacing between adjacent fibers is between about 30 micrometers and about 55 micrometers, as described in EXAMPLE 8.

In some embodiments, the scaffold for a skeletal muscle substitute comprises between 1 and 20 layers (such as between 5 and 10 layers). The spacing between layers in the scaffold may be between about 10 micrometers to about 200 micrometers, such as between about 60 micrometers and 160 micrometers or between about 80 micrometers and about 120 micrometers. In some embodiments, the layers of arrays have a spacing of between about 20 micrometers and 80 micrometers.

Typically, the scaffold is coated with an adhesion-enhancing agent before culturing cells on the scaffold to promote cell adhesion, as described in EXAMPLE 8.

In the second step in the formation of muscle substitutes of the invention, cells are cultured on the microfiber scaffold to form a muscle substitute. The scaffold directs the adhesion and behavior of cells to produce a muscle substitute having a substantially similar architecture and function as natural muscle tissue. Typically, the cells used for forming a skeletal muscle substitute comprise muscle cells, such as myoblast cells or primary cells from skeletal muscle. For use in humans, such as repair of congenital diaphragmatic hernia, autologous cells may be obtained, for example from skeletal-muscle biopsies (Fauza et al. (2001) *J. Pediatr. Surg.* 36:146) or possibly amniotic fluid (Kaviani et al. (2001) *J. Pediatr. Surg.* 36:1662). Cells used for forming a cardiac muscle substitute typically comprise cardial cells.

Figure 10A:
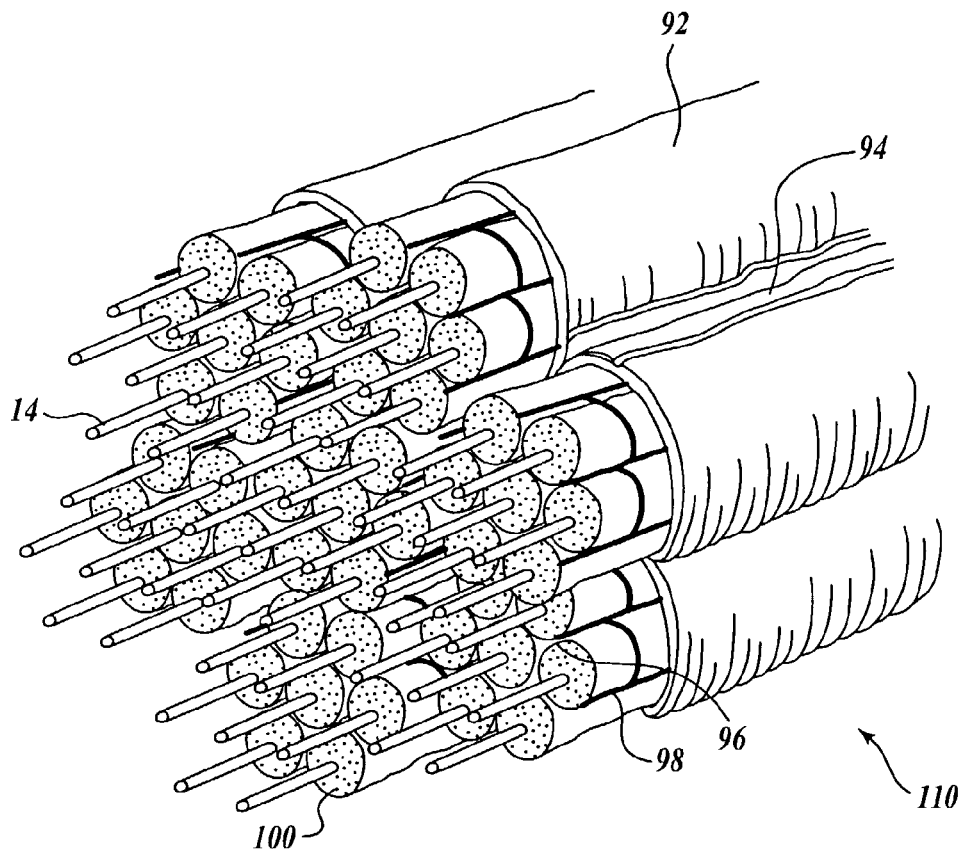
FIGS. 10A and B show views of a skeletal muscle substitute of the invention 110.

Schematic drawings of exemplary skeletal muscle substitutes are shown in FIG. 10. FIG. 10A shows a 3-dimensional array of microfibers 14, which mimic the orientation of muscle fibers in skeletal muscle tissue, and layers of muscle cells or fibers 100 in the skeletal muscle substitute. The cells, for example, myoblast cells, multiply along the microfibers 14 and orient themselves parallel to the microfibers.

The muscle substitutes may be periodically turned or rotated during culture. In some embodiments, cells are cultured on the microfiber scaffold in the presence of dynamic mechanical conditioning, as described above. It has been found that mechanical conditioning of skeletal muscle cells in culture leads to an increase in alignment and force production (Vandenburgh et al. (1991) *FASEB J.* 5:2860; Segurola et al. (1998) *In Vitro Cell Dev. Biol. Anim.* 34:609; Powell et al. (2002) *Am. J. Physiol. Cell Physiol.* 283:C1557).

Using the methods of the invention, large sheets of contracting skeletal muscle substitutes may be formed and kept alive for an extended period of time, as described in EXAMPLE 8. Myotubes increase in length and thickness over time, resulting in stronger contractions. Myotubes are well aligned along the longitudinal axis. Thus, highly structured skeletal muscle substitutes may be bioengineered by culturing muscle cells on arrays of microfibers. As shown in EXAMPLE 8, myoblast cells may be cultured in a parallel-oriented manner from a very early stage of culture, by using the geometry of the scaffold. The scaffold provides initial guidance and mechanical support. The design of the muscle substitute is largely based on cell-cell contact. This contact allows the cells to produce their own ECM and form intercellular connections, which may provide muscle substitutes with higher contractility. The adhesion-enhancing agent-coated microfibers provide spatial guidance, similar to the basement membrane in natural muscle fibers.

The skeletal muscle substitutes of the invention may further comprise other cell types, such as fibroblasts. Fibroblasts are known to promote the formation of basal lamina on the surface of myotubes (Sanderson et al. (1986) *J. Cell Biol.* 102:740). Previous studies revealed that fibroblasts were necessary for the formation of myooids (3-dimensional skeletal muscle constructs) (Dennis et al. (2001) *Am. J. Physiol.* 280: C288). It has been observed that, using primary cultures, fibroblasts orient themselves around the periphery and along the total length of myooids (Dennis & Kosnik (2000) *In Vitro Cell. Dev. Biol. Anim.* 36:327). This feature in the fiber-array approach may be used to design muscle substitutes organized in fascicles with the formation of epimysium and perimysium. This may be achieved by seeding a mixed population of myoblasts and fibroblasts onto the fibers or by seeding fibroblasts into the construct after formation of muscle-cell layers around the fibers. By seeding different cell types (e.g., myoblasts and fibroblasts) onto the scaffold for forming a muscle substitute, a natural organization into fibers and fascicles is achieved.

Figure 10B:
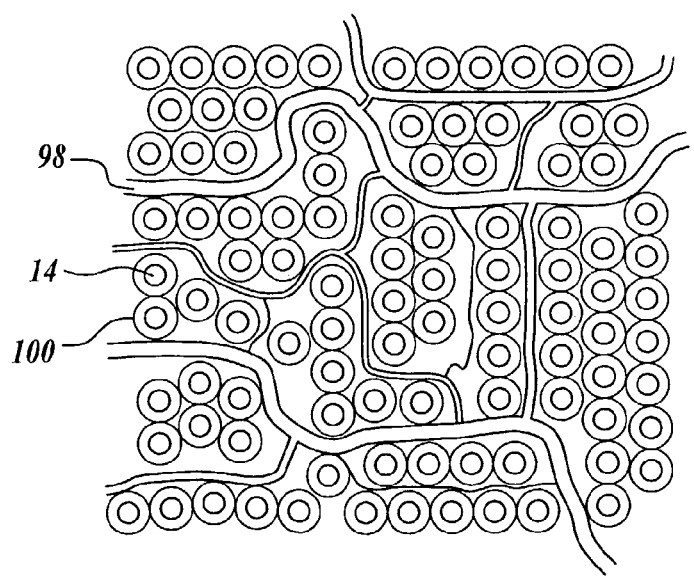
FIG. 10B is a sectional view to show that the fiber spacing may be controlled to induce the fusion of cell layers in some areas and leave gaps in other areas for the ingrowth or insertion of vasculature.

Larger 3-dimensional scaffolds may be made by several methods. For example, fibers may be arranged in many layers and in different spacing before cell seeding, as shown in FIG. 10B. Such a "smart" scaffold with small gaps and channels would allow perfusion with growth medium while in culture. This is expected to be especially successful in conjunction with mechanical conditioning, creating a pumping effect. This method leaves an opportunity for ingrowth or insertion of vasculature and nerves. An alternative approach is to create single-muscle sheets on 2-D arrays of microfibers that can be stacked on top of each other before, or during, implantation. This approach gives the possibility of placing host vasculature or independent perfusion systems in between the sheets, avoiding necrosis in the center of the construct.

In yet other embodiments, the methods of the invention can be applied to bioengineer tissue substitutes for other target tissues and organs in the body, including but not limited to, spinal cord, nerves, bone, cartilage, ligaments, tendons, heart valves, esophagus, cervix, bladder, skin, fascia, and other tissues. The methods comprise (a) providing a scaffold comprising one or more arrays of controlled-diameter microfibers, wherein at least one of the arrays is designed to mimic the configuration of one or more structural elements in the target tissue, and (b) culturing cells on the scaffold to form a target tissue substitute. A few illustrative embodiments of target tissue substitutes are described below.

Figure 11:
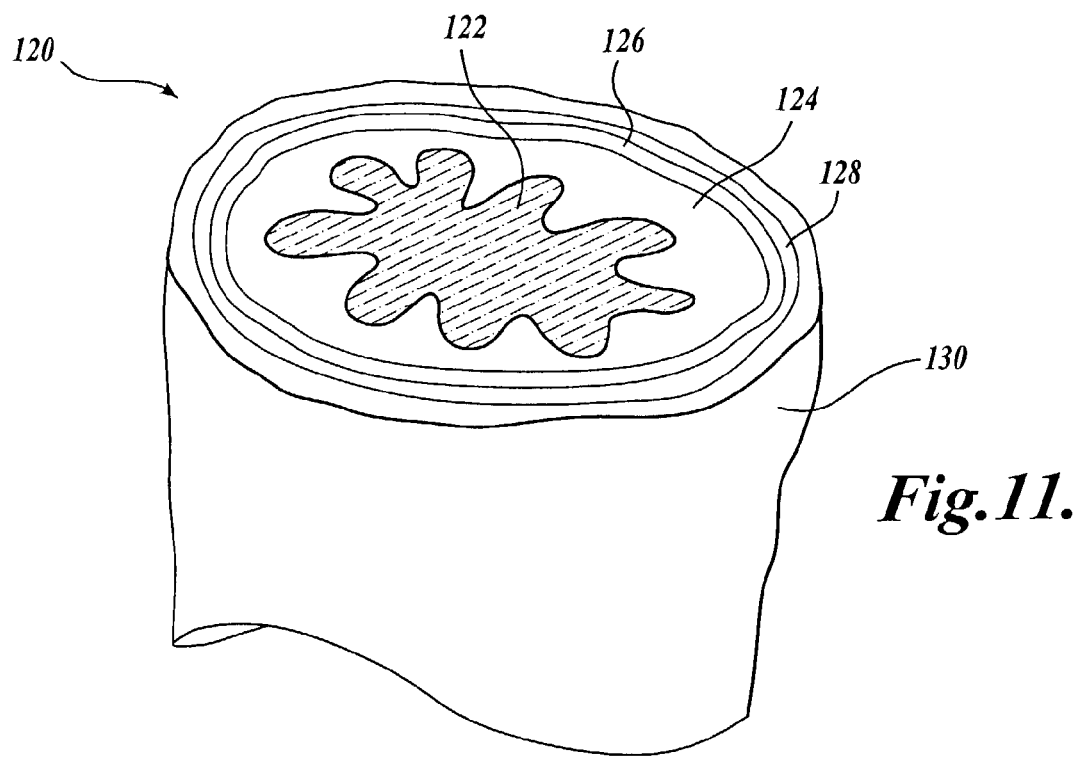
FIG. 11 shows a view of the esophagus 120. The esophagus 120 consists of several layers surrounding a lumen 122: the mucosa 124, the muscularis externa 126/128, and the adventitia 130. The muscularis externa is composed of two layers, an inner layer in which the muscle fibers are oriented circumferentially 126 and an outer layer in which the muscle fibers are aligned with the long axis of the esophagus.
Figure 12:
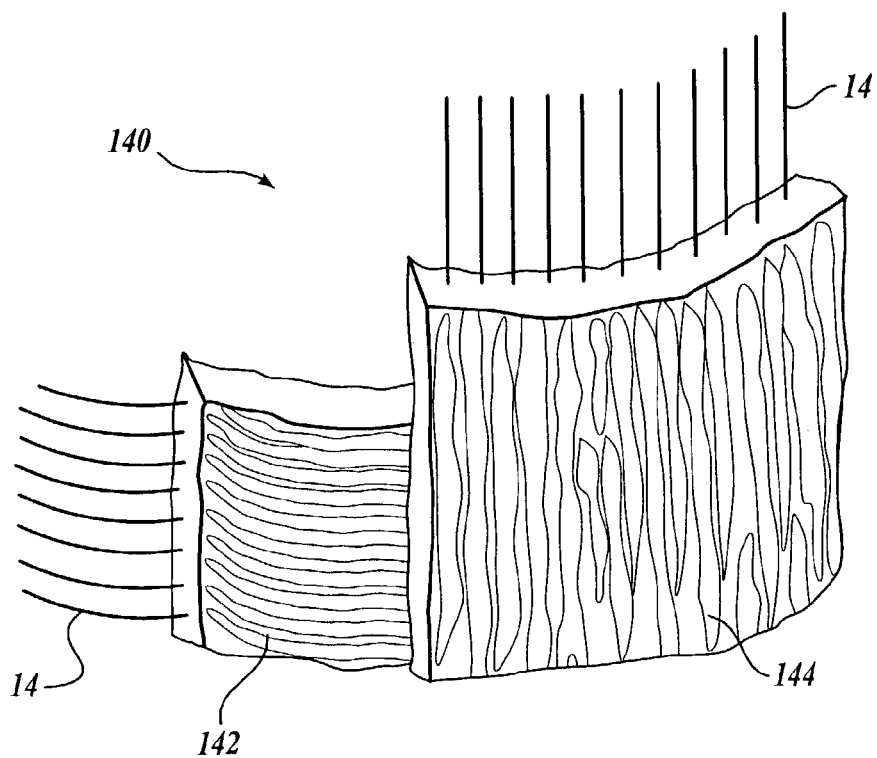
FIG. 12 shows a view of an esophagus substitute 140. In one inner part of the scaffold 142, the microfibers 14 in the scaffold are arranged to mimic the orientation of muscles fibers in the circumferential muscle layer 126, in the outer part of the scaffold 144, the microfibers 14 are arranged to mimic the orientation of the muscle fibers in the longitudinal muscle layer 128.

FIG. 11 shows the arrangement of muscle fibers in the esophagus. The esophagus 120 consists of several layers surrounding a lumen 122: the mucosa 124, the muscularis externa 126/128, and the adventitia 130. The muscularis externa is composed of two layers, an inner layer in which the muscle fibers are oriented circumferentially 126 and an outer layer in which the muscle fibers are aligned with the long axis of the esophagus. Thus, in a method for forming an esophagus substitute, the scaffold may comprise at least two layers of arrays of microfibers, wherein at least one array of microfibers is designed to mimic the configuration of the muscle fibers in the longitudinal muscle layer in the muscularis externa of the esophagus and at least one array of microfibers is designed to mimic the configuration of the muscle fibers in the circumferential muscle layer in the muscularis externa. Cells are cultured on the microfiber scaffold to form an esophagus substitute. Typically, the cells in this embodiment comprise muscle cells. FIG. 12 shows a view of an esophagus substitute 140. In one inner part of the scaffold 142, the microfibers 14 in the scaffold are arranged to mimic the orientation of muscles fibers in the circumferential muscle layer 126, in the outer part of the scaffold 144, the microfibers 14 are arranged to mimic the orientation of the muscle fibers in the longitudinal muscle layer 128.

Figures 13A, 13B:
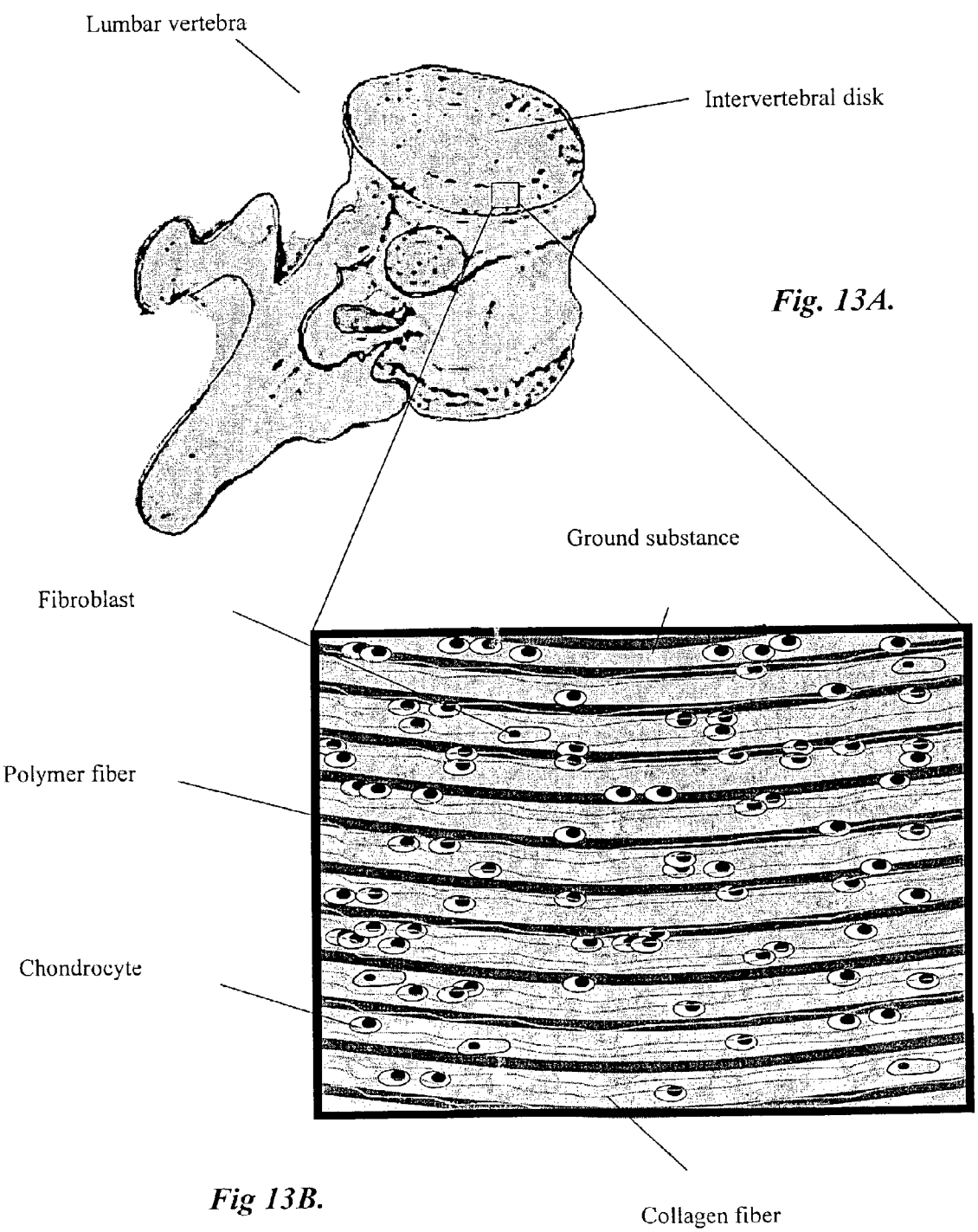
FIGS. 13A and B show two views of fibrous cartilage typical for intervertebral disks. Fibrous cartilage consists of chondrocytes that appear in short rows or clusters. The chondrocytes are embedded in ground substance and surrounded by collagen fibers that are oriented parallel to the stress lines.
FIG. 13B shows a higher magnification view of cartilage, illustrating the arrangement of collagen, fibroblasts, and chondrocytes in cartilage. Superimposed on this view is an array of microfibers of a scaffold for a cartilage substitute. The microfibers in the scaffold mimic the mechanical properties of collagen fibers until sufficient collagen is produced by the cells of the cartilage substitute.

As shown in FIG. 13, fibrous cartilage consists of chondrocytes that appear in short rows or clusters. The chondrocytes are embedded in ground substance and surrounded by collagen fibers that are oriented parallel to the stress lines. In an illustrative embodiment of a method for forming a cartilage substitute, the scaffold may comprise one or more layers of one or more arrays of microfibers, wherein the array of microfibers is designed to mimic the configuration of collagen fibers in fibrous cartilage tissue. Cells are cultured on this scaffold to form a cartilage substitute. Typically, the cells in this embodiment comprise chondrocytes. The cells in this embodiment may further comprise fibroblasts. An exemplary cartilage substitute is shown in FIG. 13B, illustrating the array of microfibers of a scaffold and the arrangement of collagen, fibroblasts, and chondrocytes in cartilage. The microfibers in the scaffold mimic the mechanical properties of collagen fibers until sufficient collagen is produced by the cells of the cartilage substitute.

Figure 14A:
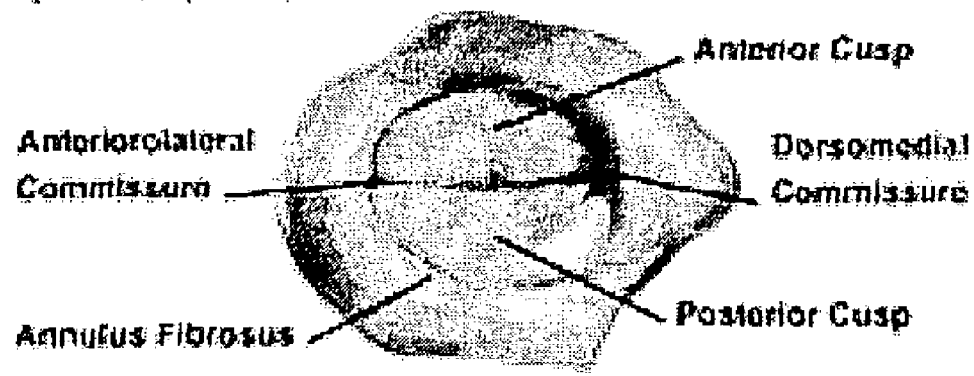
FIGS. 14A and B show two views of a mitral heart valves.
Figure 14B:
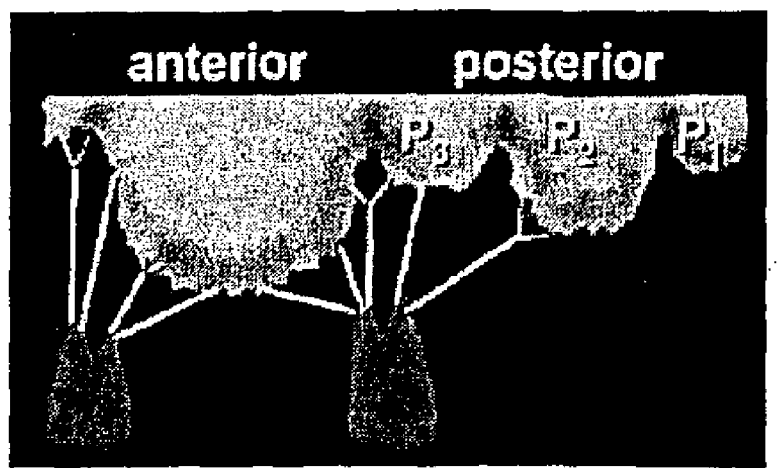
FIG. 14B shows a schematic drawing of the resected valve cusps, papillary muscles, and annulus fibrosus. The annulus is bisected at the anterolateral commissure and the cusps are spread flat (Duke University Medical Center, 2000).
Figure 15A:
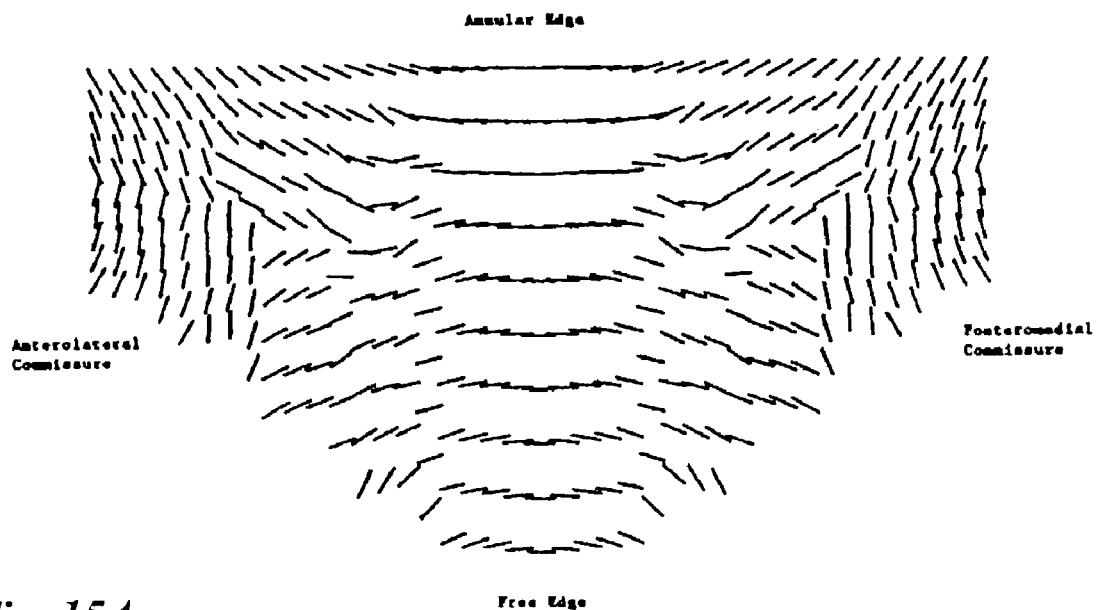
FIGS. 15A and B show the arrangement of collagen fibers in the anterior mitral valve cusp (A) and the arrangement of microfibers in a scaffold for a mitral valve substitute (B). Schematic representation of the collagen architecture in the anterior mitral valve cusp. Each line segment in (A) indicates the orientation of the collagen fibers in that region of the cusp (Cochran et al. (1991) *ASAIO Trans.* 37(3):M447-8).
Figure 15B:
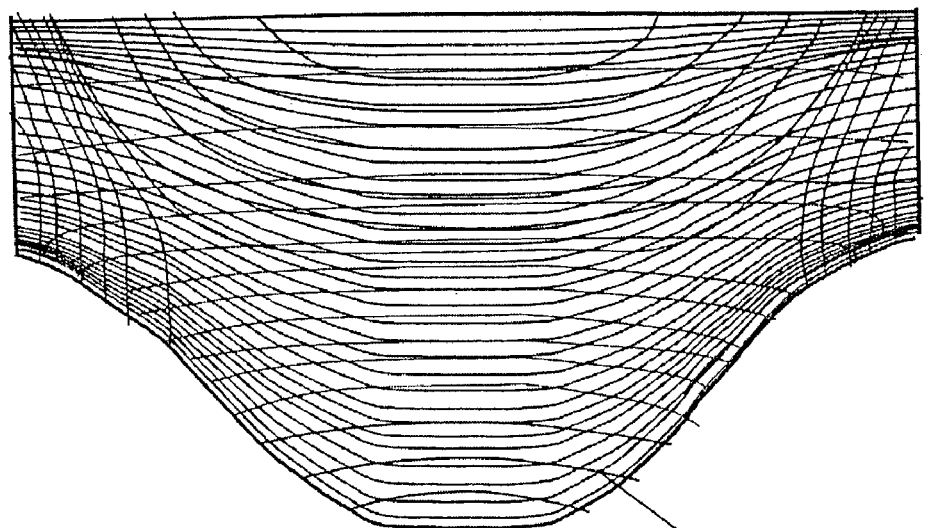

Schematic drawings of a mitral heart valve are shown in FIG. 14. The arrangement of collagen fibers in the anterior mitral valve cusp is shown in FIG. 15A. In an illustrative embodiment of a method for forming a mitral heart valve, the scaffold may comprise one or more layers of a plurality of arrays of microfibers, wherein the plurality of arrays of microfibers mimic the configuration of collagen fibers in the mitral heart valve. An exemplary arrangement of microfibers in a scaffold for forming a mitral valve substitute is shown in FIG. 15B. Cells, such as interstitial valvular cells, fibroblasts, smooth muscle cells, and endothelial cells, may be cultured on this microfiber scaffold to form a mitral heart valve substitute.

The design principles of the methods of the invention may be applied to a variety of other bioengineered tissue substitutes. The use of microfiber arrays may be adapted to direct the migration, proliferation, and differentiation of many different cell types. For example, neurons may be guided along specific axes of a microfiber array to produce nerves. Thus, the microfiber arrays may be designed to replicate the natural environment for tissue repair, for example, repair of injury to the spinal cord or peripheral nerves. The methods of the invention may also be used for the repair of bone. A scaffold in which the microfiber arrays mimic the natural bone healing environment may be designed to induce osteoblasts and osteoclasts to build a substitute bone segment. A microfiber array may also be designed to guide the behavior of cardiac myocytes to effect the replacement or repair of damaged heart muscle tissue. In addition, diaphragm substitutes may be formed using the methods of the invention to treat aplasia of the diaphragm in newborns. Using co-culture method (skeletal muscle cells and fibroblasts), tendon-like structures at the end of the fibers can be created. The methods of the invention may also be used to create ligament substitutes and ligament-bone interfaces. For example, scaffolds including microfibers extending out of a bone-like polymer mass may be co-cultured with fibroblasts and bone cells to generate a ligament-bone interface.

In another aspect, the invention provides implantable medical devices. As used herein, the term "a medical device", and grammatical equivalents thereof, encompasses two types of device: (a) a device that is completely or partially implanted into an animal body (such as a human body) during the course of normal operation of the device; and (b) a device that is used as a framework upon which to grow animal cells and/or tissues either in vivo or ex vivo.

The implantable medical devices of the invention comprise a scaffold comprising one or more layers of one or more arrays of microfibers, wherein one or more of the arrays of microfibers is arranged to mimic the configuration of one or more structural elements in a target tissue. Typically, cells are cultured on the scaffold to form a target tissue substitute. The microfibers typically have a diameter between about 1 micrometer and about 20 micrometer (such as between about 1 micrometers and about 15 micrometers or between about 1 micrometers and about 6 micrometers). In some embodiments, the microfibers are made of a biodegradable material that gradually transfers load from the scaffold to the target tissue substitute. Exemplary biodegradable materials are poly-L-lactic acid/polycaprolactone co-polymers, poly-caprolactone/poly-caprolactone-co-glycolide/poly-hydroxy-butyrate-co-hydroxyvalerate/urethane co-polymers, degradable polyurethane, and polyglycolic acid.

The microfibers in an array typically have a regular spacing. The spacing between adjacent microfibers in an array may be between about 10 micrometers and 100 micrometers (such as between about 30 micrometers and about 70 micrometers or about 40 micrometers and about 60 micrometers).

The one or more arrays of microfibers in the scaffold may be arranged in layers. The layers typically are regularly spaced. The spacing between the layers may be between about 10 micrometers and 200 micrometers (such as between about 60 micrometers and about 160 micrometers or between about 80 micrometers and about 120 micrometers). The microfibers scaffold may further comprise a coating comprising a cell adhesion-enhancing agent to promote the adhesion and spreading of cells. Illustrative cell adhesion-enhancing agents include, for example, fibronectin, laminin, and collagen. Cells are cultured on the scaffold to form a target tissue substitute.

In one illustrative embodiment, the implantable medical device may comprise a scaffold for forming a blood vessel substitute, as shown in FIGS. 3A and B. According to this embodiment, an array of microfibers in the scaffold is arranged to mimic the configuration of elastin in the medial layer of an arterial blood vessel. Thus, the scaffold may be a tubular scaffold comprising one or more layers of an array of microfibers. In some embodiments, the scaffold for a blood vessel substitute comprises between 2 and 25 layers (such as between 3 and 10 layers)

In some embodiments, the medical devices further comprise cells cultured on the scaffold to form a blood vessel substitute. The cells cultured on a scaffold for a blood vessel substitute may comprise smooth muscle cells. The blood vessel substitutes of the invention may further comprise endothelial cells. In some embodiments, the implantable medical devices comprise blood vessel substitutes, formed using three layers of microfibers, that exhibit a burst pressure of more than 1500 mm Hg after 2 weeks of culture in the absence of mechanical conditioning, as shown in FIG. 8. In some embodiments, the implantable medical devices of the invention comprise blood vessel substitutes exhibiting a burst pressure of more than 3000 mm Hg, as shown in FIGS. 7C and 8.

In another illustrative embodiment, the implantable medical device may comprise a scaffold for forming a muscle substitute, such as a skeletal muscle subsitute or a cardiac muscle substitute. In a scaffold for forming a muscle substitute, the arrays of microfibers in the scaffold are arranged to mimic the configuration of muscle fibers in muscle tissue. For example, in a scaffold for forming a skeletal muscle tissues, the arrays of microfibers are arranged to mimic the configuration of muscle fibers in skeletal muscle tissue, as shown in FIGS. 10A and B. Similarly, in a scaffold for forming a cardiac muscle tissues, the arrays of microfibers are arranged to mimic the configuration of muscle fibers in cardiac muscle tissue.

The scaffold for making a muscle substitute may comprise one or more layers of one or more parallel arrays of microfibers having a regular spacing. The scaffold may have between about 1 and about 20 layers (such as between 5 and 10 layers). The medical devices of this embodiment may further comprise cells cultured on the microfiber scaffold to form a skeletal muscle substitute. Typically, the cells cultured on a scaffold for making a skeletal muscle substitute comprise skeletal muscle cells, for example myoblast cells. Similarly, the cells cultured on a scaffold for making a cardiac muscle substitute comprise cardial cells, for example cardiac muscle cells. The cells cultured on a scaffold for making a muscle substitute may further comprise fibroblast cells.

In yet other embodiments, the implantable medical devices of the invention may provide scaffolds for other tissues and organs in the body, including but not limited to, spinal cord, nerves, bone, cartilage, ligaments, tendons, heart valves, esophagus, cervix, bladder, skin, fascia, and other tissues. The implantable medical devices comprise a scaffold comprising one or more arrays of controlled-diameter microfibers, wherein at least one of the arrays is arranged to mimic the configuration of one or more structural elements in the target tissue. In some embodiments, the implantable medical devices of the invention may further comprise cells cultured on the scaffold to form a target tissue substitute.

For example, in a medical device comprising a scaffold for an esophagus substitute, the scaffold may comprise at least two layers of at least two arrays of microfibers, wherein at least one array of microfibers mimics the configuration of the muscle fibers in the longitudinal muscle layer in the muscularis externa of the esophagus and at least one array of microfibers mimics the configuration of the muscle fibers in the circumferential muscle layer in the muscularis externa of the esophagus, as shown in FIG. 12. The medical device comprising a scaffold for an esophagus substitute may further comprise cells cultured on the microfiber scaffold to form an esophagus substitute. Typically, the cells in this embodiment comprise muscle cells, for example myoblast cells.

In another illustrative embodiment, the medical device comprises a scaffold for forming a cartilage substitute, as shown in FIG. 13B. According to this embodiment, the scaffold may comprise one or more layers of one or more arrays of microfibers, wherein the arrays of microfibers are arranged to mimic the configuration of collagen fibers in fibrous cartilage tissue. The medical device comprising a scaffold for forming a cartilage substitute may further comprise cells cultured on the microfiber scaffold to form a cartilage substitute. Typically, the cells in this embodiment comprise chondrocytes. The cells in this embodiments may further comprise fibroblast cells.

In a further illustrative embodiment, the medical device comprises a scaffold for forming a mitral heart valve, as shown in FIG. 15B. According to this embodiment, the scaffold may comprise one or more layers of a plurality of arrays of microfibers, wherein the plurality of arrays of microfibers mimic the configuration of collagen fibers in the mitral heart valve. The medical device comprising a scaffold for forming a mitral heart valve may further comprise cells, such as interstitial valvular cells, fibroblasts, smooth muscle cells, and endothelial cells, cultured on the microfiber scaffold to form an mitral heart valve substitute.

The following examples merely illustrate the best mode now contemplated for practicing the invention, but should not be construed to limit the invention.

EXAMPLE 1

Parallel-Fiber Scaffolds for Small Diameter Vessel Substitutes

Figure 6:
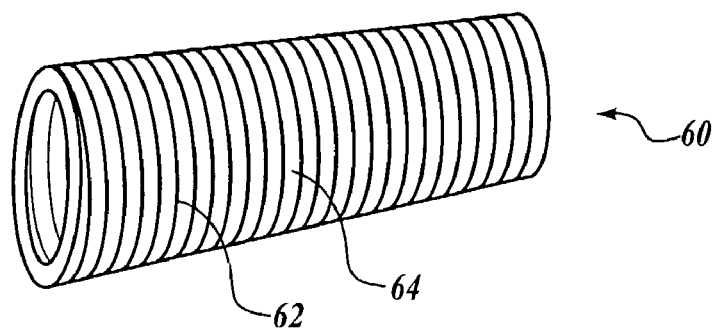
FIG. 6 shows a schematic drawing of the elastin architecture in the medial layer 60 of an arterial blood vessel. A single layer showing the helical configuration of the elastin fibers 62 is shown. There is a smooth muscle cell layer 64 between adjacent winds of the elastin fibers.

This Example describes the development of small diameter small diameter blood vessel substitutes using arrays of microfibers that mimic the arrangement of elastin fibers in the medial layer of arterial blood vessels. The arrangement of elastin fibers in the medial layer of arterial blood vessels is shown in FIG. 6.

Parallel microfiber arrays were used as scaffolds to tissue engineer the medial layer of small diameter vessel substitutes. Several questions were addressed to determine whether a parallel-fiber scaffold is a viable approach for enhancing medial layer strength and reducing the time for fabrication of vessel substitutes over current tissue-engineering methods. (1) Is an adhesive protein coating needed to attach cells to the microfibers upon seeding so as to achieve continuous cell layers between adjacent fibers? (2) Fiber spacing is likely critical to the timely formation of robust cell layers between adjacent microfibers. What spacing is optimal? (3) What strengths in the cell layer are achieved with the parallel-fiber array design and how do they compare to other tissue? Linear, parallel, microfiber arrays were used to address these questions.

Rat aortic smooth muscle cells (SMCs) were cultured on 10-micrometer diameter polypropylene fibers coated with laminin, fibronectin, or uncoated and aligned parallel to each other on rectangular mylar frames. Results showed that on laminin-coated or fibronectin-coated fibers, within 7 days cells formed continuous layers between fibers spaced at 10-20 micrometers or 40-60 micrometers but not 80-100 micrometers. However, cells at the 10-20 micrometer spacing tended to encapsulate groups of fibers and contract them into a cluster, while those at the 40-60 micrometer spacing formed uniform thickness cell layers between adjacent fibers without distorting the fiber spacing. Burst pressures of parallel-fiber constructs averaged 1686 mm Hg at 14 days, approximately 61% of that of rat intestinal mucosa.

A. Materials and Methods

Microfiber diameters of 8 to 10 micrometers were used. This microfiber diameter is consistent with the elastic lamellae sizes in natural arteries (Clark & Glagov (1985) *Arteriosclerosis* 5(1):19-34) and is a dimension that has been shown to experience minimal encapsulation in soft tissues in vivo (Sanders et al. (2000) *J. Biomed. Mater. Res.* 52:231-7; Sanders et al. (2002) *J. Biomed. Mater. Res.* 62(2):222-7). The microfibers were created using a heat and draw method. Polypropylene beads (melt index 800, Aldrich, Milwaukee, Wis.) were heated in a sterile 50-mL beaker on a hot plate to its melting point until a fiber could be drawn around a sterile test tube mounted to the shaft of a motor-driven lab stirrer (700-5400, Barnant, Barrington, Ill.). A speed of up to 10,000 RPM was used.

Linear, parallel fiber arrays were used to investigate protein coating and fiber spacing effects on construct morphology and mechanical performance. To create linear, parallel microfiber arrays, the fibers were assembled onto thin polymer frames using a custom apparatus (FIG. 2). Microfibers 14 were strung between teeth 22 of opposite-facing lice combs 24. By adjusting the positions of the combs on slide rails 26, the distances between adjacent microfibers were adjusted. Uniform spacings down to 5 micrometers were achieved. The microfibers were then sandwiched between two frames of mylar sheets (Fralock, Canoga Park, Calif.) with adhesive on their inner surfaces to keep the fibers stationary (sheet thickness 125 micrometers; inner frame dimensions 8.0×3.2 mm). Three different fiber spacings were tested on each of five frames: 10-20 micrometers, 40-60 micrometers, and 80-100 micrometers. These spacings window the range of elastic lamellae spacings in natural artery (Clark & Glagov (1985) *Arteriosclerosis* 5(1):19-34).

The frames with fibers were cleaned using RBS-35 (Pierce, Rockford, Ill.), rinsed in distilled water, then sterilized for 30 minutes on each side using ultraviolet light (UV). They were then placed in a 35-mm sterile petri dish and coated overnight at 4° C. with either a 50 micrograms/mL laminin (L2020, Sigma, St. Louis, Mo.) solution in phosphate-buffered saline (PBS), a 50 micrograms/mL fibronectin (F2006, Sigma) solution in PBS, or only PBS. Laminin and fibronectin were used because of their potential influence on neointima formation. SMCs cultured on laminin proliferate slower than SMCs cultured on fibronectin but express higher levels of smooth muscle myosin, a marker for cell differentiation (Morla & Mogford (2000) *Biochem. Biophys. Res. Comm.* 272(1):307-302), and retain a contractile phenotype for longer periods of time (Hedin et al. (1988) *J. Cell. Biol.* 107(1):307-19). Fibronectin induces a proliferative, less contractile phenotype via the Focal Adhesion Kinase (FAK) pathway (Morla & Mogford (2000) *Biochem. Biophys. Res. Comm.* 272(1):307-302). At least five frames were prepared for each group (laminin-coated, fibronectin-coated, and uncoated). After rinsing in PBS, aortic SMCs from Wistar Kyoto rats were seeded at 2.5 million cells/mL onto the arrays. The frames with fibers and cells were cultured in Dulbecco's modified Eagle's medium (DMEM, D5796, Sigma) with 4-mM L-glutamine, 1.5 g/L sodium bicarbonate, 4.5 g/L glucose (Sigma), 10% fetal bovine serum (FBS, Hyclone, Logan, Utah), 25-mM HEPES, 1-mM sodium pyruvate, 100 U/mL penicillin, and 100 microgram/mL streptomycin. Growth was visually assessed periodically using an inverted microscope.

At 7 days and 14 days, samples were prepared for light microscopy analysis. Samples were fixed in 4% paraformaldehyde, dehydrated, infiltrated, embedded with a cold curing hydroxy-ethylmethacrylate resin (Technovit 8100, Electron Beam Sciences, Inc., Agawam, Mass.) and sectioned at 5 micrometers in both the fiber cross-sections and parallel to the longitudinal axes. Sections were stained with hematoxylin and eosin or a Verhoff's stain.

As a control, an electrospun fibro-porous mesh was made with fiber diameters comparable to the arrays (less than 10 micrometers). The meshes were cleaned, sterilized, coated, and seeded using the same methods as for the microfiber arrays.

To evaluate the burst pressures of arrays, fluid pressure using PBS at 37.5° C. was applied only to the central 2-mm diameter region of the construct thus only to cells and fibers, not to the frame edge. This configuration tested the strength of cell-cell and cell-fiber attachments. During a test, the pressure was increased slowly and monitored with a pressure gauge (SLTE ST 0000, Millipore Corporation, Bedford, Mass.). Evaluations were conducted on two-layered, 10 micrometer spaced fiber arrays seeded for 7 days and 14 days.

B. Results

At 30 minutes after seeding, cell attachment was dramatically increased on fibronectin-coated and laminin-coated fibers compared to uncoated fibers (FIG. 4). Fibronectin showed slightly greater cell attachment than laminin. The cells were relatively uniformly distributed throughout the arrays at 30 minutes for protein-coated fibers, and by 2 days the cells formed layers around each fiber which thickened over the next several days. By 2 days to 7 days, depending on the fiber spacing, cell layers extended into bridges between fibers. At 10 days, the cell layers around the laminin-coated fibers appeared more uniform in thickness than those on the fibronectin-coated samples, but the differences were minor. By 3 weeks, both groups had comparable 20-40 micrometer thick layers. Cell layers on uncoated fibers were of inconsistent thickness, often balling up into clusters, presumably because without an adhesive protein coating, cellular attachment to the fibers was reduced. Cells did not bridge to form continuous layers between adjacent fibers.

Fiber spacing influenced the formation of continuous cell layers and cell alignment. Regions between fibers in the 10-20 micrometer spaced samples were completely filled with cells within 48 hours after seeding. It took between 5 days and 7 days to fill the between-fiber regions in the 40-60 micrometer samples. Arrays with 80-100 micrometer spacings had holes or gaps between the fibers that, even at 5 weeks, did not fill to form cellular layers between fibers.

Fiber spacing also influenced cellular alignment. Cells were well aligned parallel with the fiber axes for the 10-20 micrometer and 40-60 micrometer spacings. However, there was less cell alignment than for the 10-20 or 40-60 micrometer spacings, particularly near holes or gaps in the cellular bridges. Cells in those locations tended to orient with the hole edge.

Fiber spacing also influenced the contraction of the arrays. For the 10-20 micrometer spacings, cells tended to grow around and contract groups of fibers. For the 40-60 micrometer spacing, a uniform thickness cell layer formed, and the fibers remaining separated from each other, though some temporary fiber distortion due to cell traction between adjacent fibers did occur. Fibers typically returned to their original separation distance once uniform thickness cell layers were formed. At 80-100 micrometer, cells surrounded individual fibers. On rare occasions when continuous cell layers did form between fibers, they were thinner in the central region than near the fibers, and minimal array contraction occurred.

Analysis of extracellular matrix proteins elastin and collagen using a Verhoff's stain demonstrated that collagen (red) was present throughout all cell layers. Collagen fibers tended to align with the microfiber axes. Elastin (black filamentous structures) appeared mainly at the periphery, again with their axes well-aligned with the fiber axes. This elastin alignment with the microfibers is in sharp contrast to cells cultured on a flat surface, where no consistent alignment was apparent.

Unlike the microfiber arrays, results at 9 days showed that the cells in the mesh grew in a highly disorganized fashion and were not able to form an architecture resembling the arterial medial layer. There were many holes within the cell layers, and cells and collagen fibers showed no preferred orientation. Out of plane misalignment of cells occurred because the microfibers were not all in one plane.

Burst pressure measurements were conducted on 10-micrometer spaced fiber arrays seeded for 7 and 14 days. A mean pressure of 322 mm Hg (five samples tested) was required to burst the structure at 7 days, and a mean pressure of 1686 mm Hg (two samples tested) at 14 days (FIG. 7). In the cultured linear array samples, failure occurred between adjacent cells indicating that cell-fiber connections were stronger than cell-cell attachments. Testing on cell-less arrays demonstrated no pressure resistance, validating the testing method.

The 14-day result is approximately 61% of that of intestinal mucosa of Sprague-Dawley rat measured with the same test jig (two samples tested). Although natural small diameter arteries have a much higher burst pressure (~4500 mm Hg, Girton et al. (2000) *J. Biomech. Eng.* 122(3):216-23), the strength of the constructs may be considerably enhanced using multiple layers of microfiber arrays (e.g., between 7-23, consistent with the natural artery, Clark & Glagow (1985) *Arteriosclerosis* 5(1):19-34) and dynamic mechanical stimulation. The 7-day culture result of a burst pressure of 308 mm Hg approaches that of 436 mm Hg achieved with a collagen-based construct after 2 days of culturing and 8 days of dynamic stimulation (Seliktar et al. (2000) *Ann. Biomed. Eng.* 28(4):351-62).

EXAMPLE 2

Vessel Substitutes Formed with Tubular Scaffolds

This Example describes the development of vessel substitutes using tubular scaffolds made from arrays of microfibers that mimic the arrangement of elastin fibers in arterial blood vessels. The experiments described here address the question of whether concentric helices of microfibers be assembled into a scaffold, and if so what strengths may be achieved in a bioengineered, vessel substitute medial layer using such a scaffold. A tubular construct made using concentric helices of 10-micrometers diameter fibers as a scaffold showed elastin fibers aligned with the microfibers at 7 days, with a dense elastin network at 33 days. The burst pressure of the blood vessel substitute at 80 days averaged 3372 mmHg.

A. Materials and Methods

Tubular scaffolds was created by wrapping concentric layers of microfibers around a mandrel (a thin candy cane), stabilized with longitudinal fibers and end rings. The microfiber arrays were constructed using a 3.9-mm diameter sugar rod as a mandrel. A single 8 to 10 micrometer polypropylene fiber was wound into a helix onto the surface of the mandrel. To facilitate fabrication speed, first a long 10-fiber ribbon was made using the apparatus shown in FIG. 2. The ribbon was then wrapped around the sugar rod using a drill chuck that allowed manual advancement of the ribbon. Fiber-to-fiber spacing averaged 50 micrometers though some adjacent winds were spaced as high as 100 micrometers because of resolution limits of the manual system. Once a single layer was completed then five nylon spacer fibers (125-micrometers diameter), oriented longitudinally with the mandrel axis, were glued (6060, 3M, St. Paul, Minn.) to the wound fiber, and another single fiber layer wrapped around that structure. Another group of five spacer fibers was then added and another single fiber layer wrapped around that structure, so that there were a total of three fiber layers, each separated by 125 micrometers. The structure was 33 mm in length. The construct was then put in nanopure water for 10 min to dissolve the sugar rod, and then cleaned in RBS-35, rinsed in distilled water, then sterilized for 30 minutes on each side using UV.

The tubular scaffolds were coated with laminin as described in EXAMPLE 1, and was cultured in the same media as that used for the linear arrays at a rat aortic SMC cell concentration of $3 \times 10^6$ cells/mL. Media changes were made every third day. At days 7, 14, and 33, segments of the vessel substitute were cut from the ends, fixed, and prepared for light microscopy using an elastin stain, as described in EXAMPLE 1. At 7, 14, and 80 days, segments of the blood vessel substitute were removed, flattened out, then cut to a 12-mm diameter for testing in the burst pressure system. Several samples were evaluated for burst pressure as described in EXAMPLE 1.

B. Results

After culture of the tubular scaffolds of microfiber arrays, a continuous medial-layer substitute wall formed within 5 days. Elastin fibers formed quickly between aligned cells and were oriented parallel with the fiber axes by 7 days. Elastin density increased at 14 days and was substantial by 33 days. The wall thickness was thin in some locations of the tissue substitute, which was probably a result of the resolution limits of the manual fiber-winding apparatus. Large between-fiber spaces in the tubular construct required over 40 days to develop a thickness comparable to the rest of the structure, consistent with results from the 80-100 micrometer spacing experiments using the linear microfiber arrays.

The burst pressure of the blood vessel substitutes increased over time (FIG. 8). The burst pressure at 80 days averaged 3372 mm Hg for the samples tested (FIGS. 7C and 8). Target burst pressures are at least 1680 mm Hg, comparable to that of the saphenous vein, which has been used for coronary artery repair. Over time in vivo, the construct should develop strength comparable to small diameter arteries. After 14 days, the burst pressure of the vessel substitute was comparable to that of other tissue-engineered constructs after at least 56 days in culture (Nerem & Seliktar (2001) *Annu. Rev. Biomed. Eng.* 3:225-43; Niklason et al. (1999) *Science* 284(5413): 489-93; L'Heureux et al. (1998) *FASEB J.* 12(1):47-56). These results were obtained without mechanical conditioning, a technique that further enhances construct strength. Thus, the vessel substitutes of the invention achieve sufficient burst strength after less than 2 weeks of culture.

EXAMPLE 3

Mechanical Properties of Degradable Polymers for Microfiber Scaffolds

This Example describes the evaluation of mechanical properties of four different degradable polymers for microfiber scaffolds.

The ideal material for the microfiber scaffold has the following features: (a) it induces good cell adhesion and spreading upon seeding, facilitating the production and assembly of extracellular matrix proteins; (b) it has degradation byproducts that are not problematic in vivo; (c) it has an initial modulus comparable to or slightly greater than that of elastin, and that reduces over time to effectively transfer load to the bioengineered structure as is matures, and (d) the material is easily manufacturable into different architectures.

Although initially it would seem logical to use elastin as the scaffold, it is not appropriate for several reasons. The design philosophy is to transfer mechanical load from the substrate to the bioengineered construct as it matures. It is unlikely elastin will have an appropriate degradation rate to achieve this goal, and the degradation rate cannot be adjusted. In addition, SMCs have a greater proliferative rate when in contact with collagen or fibronectin than elastin (Wilson et al. (1995) *J. Clin. Invest.* 96(5):2364-72). Other studies have demonstrated that elastin coatings induce almost a 4-fold increase in apoptosis compared with collagen, fibronectin, and laminin, suggesting that collagen, fibronectin, and laminin provide a significant survival signal that elastin does not (Freyer et al. (2001) *Am. J. Respir. Cell Mol. Biol.* 25(5):569-76). These disadvantages of elastin may be overcome by producing a recombinant elastin protein that eliminates the undesirable properties of elastin while retaining its desirable properties. Using genetic engineering and microbial protein expression (McMillan et al. (1999) *Macromolecules* 32:3643-48; McMillan et al. (2000) *Macromolecules* 33:4809-21), an 81 kDa recombinant protein was produced (Huang et al. (2000) *Macromolecules* 33:2989-97) based on the repeating elastomeric peptide sequence of elastin (Val-Pro-Gly-Val-Gly)$_4$(Val-Pro-Gly-Lys-Gly) (Urry (1988) *J. Prot. Chem.* 7(1):1-34)

The mechanical properties of four different degradable polymers were investigated:

LP: 75% poly-L-lactic acid (L-PLA)/25% poly-caprolactone (PCL) copolymer;

DP: 75% poly-DL-lactic acid (DL-PLA)/25% poly-caprolactone (PCL) copolymer;

PPPU: 93% poly-caprolactone (PCL)/poly-caprolactone-co-glycolide (PCL/PGA)/poly-hydroxybutyrate-co-hydroxyvalerate (PHBV)/7% urethane co-polymer; and Degradable polyurethane: composition not disclosed (from K A Woodhouse, U Toronto).

The basis for using these four materials is that they are degradable with a relatively low modulus, comparable to that of elastin, the protein that the material is intended to mimic mechanically. LP, DP, and PPPU were available commercially (Alkermes (Cincinnati Ohio); ETH Materials (Zurich, Switzerland)). Degradable polyurethane was available from a collaborator (K A Woodhouse, University of Toronto).

Heat and draw methods were used to make microfibers ranging from 8 to 13 micrometer in diameter. The polymer was heated in a sterile 50-ml beaker on a hot plate until a fiber could be drawn around a sterile test tube mounted to the shaft of a motor-driven lab stirrer. The motor was operated at up to 10,000 RPM depending on the polymer. All materials except the degradable polyurethane could be easily fabricated. The degradable polyurethane changed its structure when brought above 40° C. and was no longer degradable. To overcome this limitation, it was solution-drawn using N,N-dimethylacetamide (DMAC) as a solvent. However, there were problems in drawing consistent-diameter long fibers, and the material exhibited plastic deformation just with simple handling. This material was thus not tested or used further. All other materials did not undergo changes in structure, and were stored in a desiccator before testing.

Figure 16:
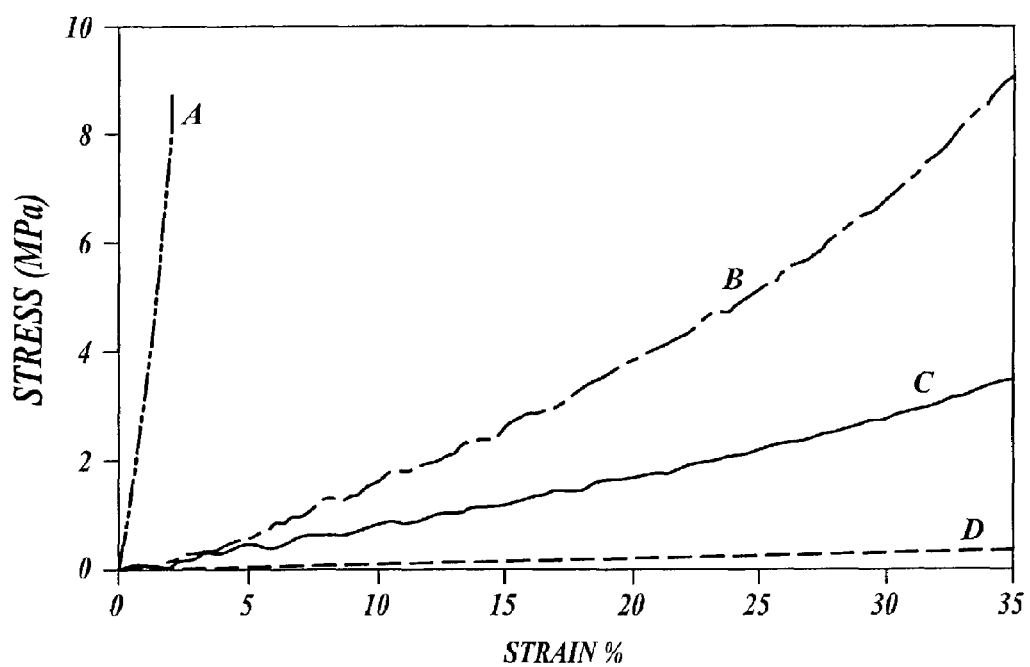
FIG. 16 shows a chart documenting the stress/strain plots of collagen (A), elastin (D), and candidate polymers PPPU (B) and LP (C).

Single fibers of each polymer were tested in a custom microtensile device (Sanders et al. (2002) *J. Biomed. Mater. Res.*, submitted). The device had a force resolution of 0.6 micronewton and a displacement resolution of 0.02 micrometers. Fibers were mounted and clamped at the ends to vertical rods using a jig that ensured they were well aligned with the load axis and not strained during mounting. One vertical rod connected to a load cell and the other to a linear slide rail. Fibers were submerged in a water bath maintained at 37.5° C. during testing using 2 high-density cartridge heaters (McMaster-Carr, Los Angeles, Calif.) under PID control (CNi32D33, OmegaEngineering, Stamford, Conn.). The temperature in the bath did not deviate by more than 0.5° C. A 0.05% aqueous solution of non-ionic wetting agent (DeIONIC LF-EP-40, DeForest Enterprises, Inc., Boca Raton, Fla.) in nanopure water was used in accordance with ASTM standards (Test Methods for Textile Fabrics, ASTM D5034-95 and D5035-95). The wetting agent reduced the surface tension of the water and prevented undue strain on the fiber as it was being submerged. Strain was applied at a rate of 2 mm/second or until the extension limit of the lead screw was reached. Testing of the microfibers showed material properties closer to that of elastin than collagen (FIG. 16). LP and PPPU showed consistent results from fiber to fiber, unlike DP, which showed tremendous variability. The high variability is consistent with the "DL" as opposed to the "L" configuration of the polymer. The mean modulus of DP was less than that of elastin. It is important to note, however, that DP will degrade much more quickly than LP because it is less crystalline.

These results are encouraging in that material properties comparable to that of elastin can be achieved with these co-polymers. Microfiber tubular arrays using these materials are assembled, as described in EXAMPLE 2, and their mechanical properties are tested and compared to the properties of arteries reported in the literature (Sato et al. (1979) *Med. Biol. Eng. Comput.* 17(2):170-6; Hayashi (1993) *J. Biomech. Eng.* 115(4B):481-8; McVeigh et al. (2002) *Clin. Sci.* (Lond.) 102(1):51-67).

EXAMPLE 4

Protein Coating of Microfibers

This Example describes the coating of microfibers made from candidate polymers with a cell adhesion-enhancing protein to achieve good cell adhesion and spreading after seeding.

Two polymers are used for the degradable scaffolds: LP: poly-L-lactic acid (LPLA)/poly-caprolactone (PCL) copolymer; and PPPU: poly-caprolactone (PCL)/poly-caprolactone-co-glycolide (PCL/PGA)/poly-hydroxybutyrate-co-hydroxyvalerate (PHBV)/urethane co-polymer. The basis for selection of these polymers is that their compositions can be controlled to tailor both the mechanical properties (modulus) and the degradation rates, and they are available commercially in a customized form. In addition, they are easily manufacturable into microfibers of uniform thickness, as shown in EXAMPLE 3. The microfiber scaffolds are assembled using LP and PPPU fibers and a fiber spacing of 20-40 micrometers, as described in EXAMPLE 1.

Three candidate cell adhesion-enhancing proteins are used to achieve good cell adhesion and spreading upon seeding: (1) fibronectin; (2) laminin; and (3) collagen. Good cell adhesion and migration was obtained with both fibronectin-coated and laminin-coated fibers, as described in EXAMPLE 1 (FIG. 4). Collagen is also a candidate because of its abundance and close apposition to SMCs and its extensive use as a natural scaffolding material (Cavallaro et al. (1994) *Biotechnol. Bioeng.* 43:781-91; Li (1995) *The Biomedical Engineering*

Handbook (Brozino ed.) Boca Raton, Fla., CRC Press, pp.627-647). It has been shown to induce smooth muscle cell adhesion (Naito et al. (1992) *Atherosclerosis* 96(2-3):227-34; Hayward et al. (1995) *Cell Biol. Int.* 19(10):83946), enhance proliferation of SMCs in the presence of platelet derived growth factor (Hirst et al. (2000) *Am. Respir. Cell. Mol. Biol.* 23(3):335-44), and produce greater collagen and elastin expression in SMC than fibronectin (Kim et al. (1999) *Exp. Cell Res.* 251(2):318-28). It may be an important anti-apoptotic element (Freyer et al. (2001) *Am. J. Respir. Cell. Mol. Biol.* 25(5):569-76). The form of the collagen coating, monomer or polymerized, will affect the cell behavior (Bacakova et al. (1997) *Ex. Mol. Pathol.* 64(3):185-94; Pickering (2001) *Circ. Res.* 88(5):458-9). The monomer form of collagen is used as it supports SMC proliferation whereas polymerized collagen inhibits proliferation (Koyama et al. (1996) *Cell* 87(6):1069-78; Ichii et al. (2001) *Cir. Res.* 88(5):460-7; Pickering (2001) *Circ. Res.* 88(5):458-9). Polymerized collagen can induce the expression of metalloproteinases, which would break down the structure (Ravanti et al. (1999) *J. Biol. Chem.* 274(4):2446-55; Mauch et al. (1989) *FEBS Lett.* 250(2):301-5).

To apply the monomer collagen coating, the arrays are washed, soaked in 0.5% acetic acid for 20 minutes at 60° C., rinsed with distilled water, and incubated with 0.1 mg/ml collagen I (Vitrogen 100, Cohesion, Palo Alto, Calif.) for at least 3 hours at room temperature. They are then rinsed with PBS (Sigma, St. Louis, Mo.).

After cleaning with RBS-35 and distilled water then sterilizing using UV, the arrays are coated with the three coatings (fibronectin, laminin, collagen). The fibronectin and laminin coatings will be applied overnight at 4° C. with the coating protein in solution, as described in EXAMPLE 1. Since collagen is not as adhesive as laminin (Langer & Vacanti (1999) *Sci. Am.* 280(4):86-9), plasma-coating of the collagen onto the fibers may be used (Dr. Ratner, Director UWEB, Bioengineering and Chemical Engineering, University of Washington, Seattle).

EXAMPLE 5

In Vivo Tissue Response to Degradable Polymers

This Example describes the in vivo response to the degradable polymers used in the microfiber arrays of the invention.

The degradable polymers, configured in the proposed architectures at the candidate compositions, are evaluated to assess whether they are detrimental to tissues in vivo, for example, by causing smooth muscle cell death, fibroblast migration into the construct, or fibrous encapsulation of individual microfibers in vivo. Two mechanisms for causing detrimental effects are possible: (1) the polymers, even though degradable, may be recognized as foreign material and thus initiate a foreign body response and fibrous encapsulation of individual fibers within the construct; (2) the degradation byproducts for the candidate co-polymers to be used may be detrimental to smooth muscle cell health.

Recent investigations demonstrate that fibrous encapsulation of polymer microfibers is dependent on fiber diameter. For low-modulus materials comparable to the ones used here, capsule thickness was typically zero or minimal for fibers less than ~8 micrometers, but was larger for fibers >10 micrometers diameter (Sanders et al. (2002) *J. Biomed. Mater. Res.* 62(2):222-7). This result, and the fact that the microfibers are hidden under the arterial SMCs, which have been demonstrated to be acceptable (Merrilees et al. (2002) *Circ. Res.* 90(4):481-7) make host cell ingrowth and encapsulation unlikely.

The degradation products of the PL polymers are PLA and PCL for LP, and the PPPU polymer degradation products are PCL, PGA, and PHBV, all of which have been well studied in terms of their mechanisms of degradation. PLA degrades by hydrolysis into lactic acid (Spain et al. (1998) *Tissue Eng.* 4(4):343-52), a natural precursor for the citric acid cycle that produces water and carbon dioxide excreted through respiration. Similarly, PGA degrades by hydrolysis into glycolic acid, which is excreted in the urine or can be made into serine by the body which, like lactic acid, will be degraded naturally through the citric acid cycle (Spain et al. (1998) *Tissue Eng.* 4(4):343-52). PCL degrades by hydrolysis and yields caproic acid (Corden et al. (2000) *Biomater.* 21(7):713-24), a medium-chain fatty acid. Caproic acid is transported to the liver by the bloodstream where it is metabolized like native fatty acids into carbon dioxide, acetone, or ketone bodies (Traul et al. (2000) *Food Chem. Toxicol.* 38(1):79-98). The formation of acetone and ketone bodies occurs only when fatty acids are in excessive amounts in the liver, and in general their concentrations do not reach toxic levels (Traul et al. (2000) *Food Chem. Toxicol.* 38(1):79-98). PHBV either catabolizes into carbon dioxide and water (Hankermeyer & Tjeerdema (1999) *Rev. Environ. Contam. Toxicol.* 159:1-24) or produces poly-hydroxybutyrate (PHB) particles (Camus & Neuenschwander (2001) *A New Biomaterial: DegraPol.*, Zürich, ETH Polymer Materials, Institute of Polymers), depending on the stereochemistry of the PHBV. The PHB particles are phagocytosed by macrophages, cleaved, and eliminated (Camus & Neuenschwander (2001) *A New Biomaterial: DegraPol.*, Zürich, ETH Polymer Materials, Institute of Polymers). No toxicity is reported at PHB particle concentrations less than 10 µg/ml, which indicates that controlling the degradation rate of PHBV will control the inflammatory reaction and therefore the biocompatibility (Saad et al. (1996) *J. Biomed. Mater. Res.* 30(4):429-9). Therefore, smooth muscle or host cell death from these byproducts is unlikely.

Linear parallel microfiber array architectures are used, as described in EXAMPLE 1, with multiple layers to more accurately represent the 3-dimensional tubular array. To create the 3-dimensional structure, mylar sheets (Fralock) of thickness identical to that of the desired layer spacing (60 micrometer) (minimum thickness mylar sheet available is 25 micrometers) are used for the frames. Frames are stacked, using the adhesive already on the mylar sheets for bonding. After assembly, the 3-dimensional arrays are cleaned, then coated, as described in EXAMPLE 4.

Implantation is initiated when cellular bridges have formed, expected to be 3-5 days. This selected culture interval is conservative towards the overall purpose of this study, since longer culture intervals, which may be needed to make the entire vessel substitute, would only further surround the fibers with cells, reducing the chance for cell death and fibroblast migration. Thus, if results from this test show good in vivo response, then the polymers should be acceptable for the vessel substitutes.

A Fisher (344) rat model, extensively used in transplantation experiments to circumvent the immunological barrier between donor and host individual (Reinecke et al. (1999) *Circulation* 100(2):193-202; Saxena et al. (1999) *Tissue Eng.* 5(6):525-32; Katayama et al. (1994) *Cell Transplant.* 3 Suppl. 1:S39-41) is used. Immunosuppressant injections or other medications are not needed, which is less traumatic to the animal. A total of 54 rats are used for this study, 3 animals/group (9 groups for LP, 9 groups for PPPU).

One construct is implanted subcutaneously in each rat in the lateral dorsum in the subscapular region, so that the animal cannot access the site with its teeth post-surgery. This site has previously been used to investigate the in vivo response of acellularized porcine aortic tissue (Bader et al. (2000) *Transplantation* 70(1):7-14) and to investigate the in vivo response to biomaterials (Sanders et al. (2000) *J. Biomed. Mater. Res.* 52:231-7; Sanders et al. (2002) *J. Biomed. Mater. Res.* 62(2): 222-7). A specialized technique that helps to ensure a consistent implantation procedure from animal to animal is used (Sanders et al. (2000) *J. Biomed. Mater. Res.* 52:231-7). Once the rat has been anesthetized using isofluorane inhalation, the implant region is shaved and wiped down with betadine. A 10-cc syringe (21-gauge needle) is used to inflate an air bubble subcutaneously at a depth no greater than 1.5 mm. The incision is made at the edge of the air bubble site and the implant carefully placed within the pocket created by the bubble. The incision is then closed with staples, positioned far enough from the implant site so as not to be over the implant. The location of the implanted vessel is marked continually (once a week) with ink (Sharpie™ marker) to facilitate identification of the site at the end of the experiment. Animals are housed in separate cages to reduce trauma to the implant locations.

After 5 weeks the constructs and surrounding tissue are removed. A 5-week implant interval is consistent with biomaterial testing for chronic inflammatory response. A small section of the array (4-mm thick) is taken immediately to assess the live and dead cell densities. The section is stained with 50-micromolar Calcein AM and 25-micromolar ethidium homodimer-1 (live/dead cell stain L-3224, Molecular Probes, Eugene, Oreg.) and viewed under a fluorescent microscope (Nikon Microphot-SA) (Imbert & Cullander (1999) *J. Control Release* 58(1): 39-50). Live and dead cell densities are assessed using quantitative morphological methods (Gundersen & Jensen (1987) *J. Microsc.* 147(pt 3):229-63). The rest of the tissue is immediately embedded in Tissue-Tek OCT Compound (Optimum Cutting Temperature Compound, Sekura Finetek, Torrance, Calif.). Frozen sections are taken (4-micrometer) for histological and immunohistological analysis. The presence of fibroblast cells is determined using anti-fibroblast primary antibody (ab8737, Novus Biologicals, Littleton, Colo.) (Janin et al. (1990) *Clin. Exp. Rheumatol.* 8(3):237-42) and labeled using Vectastain Elite ABC Kit (Vecta Laboratories, Burlingame, Calif.). These sections are visualized using DAB (Dako Corporation, Carpinteria, Calif.) on a Nikon Microphot-SA microscope. Densities within the arrays are assessed using quantitative morphological methods (Gundersen & Jensen (1987) *J. Microsc.* 147(pt 3):229-63). Haematoxylin and eosin stained sections are used to assess fibrous capsule presence around individual fibers as done previously (Sanders et al. (2000) *J. Biomed. Mater. Res.* 52:231-7).

A MANOVA with the variables dead cell percentage, fibroblast cell percentage, and capsule presence percentage is used to evaluate the results. If the results show that one variable dominates the analysis, then individual t-tests are used to assess the relative change of each variable and its significance.

EXAMPLE 6

Optimizing Substrate Modulus and Degradation Rate During Dynamic Mechanical Conditioning This Example describes the optimization of substrate modulus and degradation rate of two different degradable polymers during dynamic mechanical conditioning. The composition of two co-polymers, LP and PPPU, are selected to effectively transfer loads from the microfiber scaffold toe the SMC-elastin-lamellar structure in vitro to achieve natural artery material properties and burst strengths.

The co-polymer compositions are optimized to match the desired natural artery modulus. A reduction in modulus over time, achieved by controlling the material degradation rate, is desirable so that the tissue-engineered construct takes up more of the load as it matures. At a very low substrate degradation rate and high modulus, no load will be transferred to the tissue and, therefore, no strengthening will occur. At a very fast substrate degradation rate and low modulus, the tissue will quickly be overloaded and the structure will rupture.

It is important to note that degradation rate is optimized only in the sense of adjusting the modulus over time. The extended presence of the scaffold in vivo is not relevant as long as it does not affect the vessel substitute mechanical properties. Given the small dimensions of the fibers, a chronic inflammatory response to them is not expected (Sanders et al. (2002) *J. Biomed. Mater. Res.* 62(2):222-7).

Substrate compositions with 3 degradation rates ($R_1$, $R_2$, $R_3$) with 3 moduli at each rate (for $R_1$:$M_1$,$M_2$,$M_3$; for $R_2$:$M_4$, $M_5$,$M_6$; for $R_3$:$M_7$,$M_8$,$M_9$) are tested, making a total of 9 groups. If results demonstrate that intermediate or other degradation rates or moduli are appropriate, materials with those compositions are added.

To make polymers with different degradation rates and moduli, polymer compositions are adjusted. The hydrolysis of ester linkages determines the degradation rate of a co-polymer. In PPPU, the limiting factor for degradation is the percent of polyglycolic acid (PGA) (Camus & Neuenschwander (2001) *A New Biomaterial: DegraPol.*, Zürich, ETH Polymer Materials, Institute of Polymers), controlled through the concentration of the caprolactone-co-glycolide. Changing the average molecular weight and viscosity of the co-polymers may also affect the degradation rate and the modulus (Spain et al. (1998) *Tissue Eng.* 4(4):343-52). Polymers composed of a range of inherent viscosity values lose mass and strength at a lower rate than those with a single inherent viscosity value do (Spain et al. (1998) *Tissue Eng.* 4(4):343-52). The LP co-polymer will have a lower degradation rate because it is more crystalline, which limits water penetration into the polymer. However, some adjustment is possible.

Mechanical properties can also be controlled through compositional changes. For example, poly-lactic acid (PLA) provides mechanical strength (Mooney et al. (1996) *Biomater.* 17(2):115-24), while poly-caprolactone increases elasticity (Camus & Neuenschwander (2001) *A New Biomaterial: DegraPol.*, Zürich, ETH Polymer Materials, Institute of Polymers; Alkermes Medisorb Bioabsorbable Polymers (2001) General Mechanical Properties). Thus, in the LP co-polymer, the ratio of lactone to caprolactone will determine mechanical properties. LP composition with ratios from 60%/40% and 85%/15% are tested. For the PPPU co-polymer, adjustment of the ratios among poly-caprolactone, poly-caprolactone-co-glycolide, and poly-hydroxybutyrate-co-hydroxyvalerate are made to provide a range of moduli.

Tubular constructs are fabricated for each of 9 co-polymer designed to achieve optimal material modulus/degradation rate combinations. With two co-polymers, LP and PPPU, a total of 18 designs are tested.

Tubular constructs are fabricated, for example as described in EXAMPLE 2. A microfiber diameter of ~8 micrometers is used, a dimension shown for low-modulus materials to induce minimal encapsulation in soft tissue in viva (Sanders et al. (2002) *J. Biomed. Mater. Res.* 62(2):222-7). The microfiber spacing is between 20-40 micrometers, and layers are spaced at 60-80 micrometers. Ten layers are generated, consistent with internal mammary artery anatomy (Canham et al. (1997) *Cardiovasc. Res.* 34(3):557-67). This results in a vessel substitute with an outer diameter of approximately 2.8 micrometers and a material to tissue ratio of 1:26.4 (3.8% material). The microfiber spacings and number of layers may be adjusted to change material properties.

The constructs are seeded with rat arterial SMCs at 2.5 million cells/ml. Each construct is put in the dynamic mechanical conditioning system shown in FIG. 5, and controlled strains are applied. Initial testing is conducted on a limited number of samples to optimize (1) the culture time intervals before initiating strain application; (2) the rate of increase in strain magnitude during initial conditioning sessions; and (3) the strain magnitude to dynamically condition the construct so as to achieve appropriate moduli and burst strengths.

In order to achieve a lamellar-like morphology, it may be desirable to wait until cellular bridges have formed between adjacent fibers (~5 days) before straining. A gradual increase in strain magnitude, used by some (Hoerstrup et al. (2001) *Eur. J Cardiothorac. Surg.* 20(1):164-9), but not others (Seliktar et al. (2000) *Ann. Biomed. Eng.* 28(4):351-62; Niklason et al. (1999) *Science* 284(5413):489-93), may be appropriate so as not to tear apart the lamellae organization. A strain magnitude between 5% and 10% applied at 1 Hz is expected appropriate, based on previous studies (Seliktar et al. (2000) *Ann. Biomed. Eng.* 28(4):351-62; Niklason et al. (1999) *Science* 284(5413):489-93, Kim et al. (1999) *Nat. Biotechnol.* 17(10):979-83). To test construct status, cell apoptosis is evaluated using an in situ apoptosis detection kit (TUNNEL assay, ApopTag, Intergen, Purchase, N.Y.). Appropriate conditions are those that induce remodeling but do not induce cell apoptosis.

The 9 constructs for each of the 2 co-polymers are evaluated at multiple time points after the initiation of strain application, assessing elastin and collagen production, vessel substitute morphology, modulus, and burst strength, as described in EXAMPLE 1. Constructs are evaluated on days 3, 6, 10, 14, and 21. It is expected that <10 days of mechanical conditioning will achieve an acceptable modulus and burst strength. Modulus may be assessed using the dynamic mechanical conditioning system because it is equipped with both strain and pressure measurement devices. Alternatively, rings of the construct may be tensile-tested using methods similar to those used previously (Seliktar et al. (2000) *Ann. Biomed. Eng.* 28(4):351-62). The burst pressure is the maximum pressure the construct can tolerate without failure and is assessed using an instrumented pressure source to apply PBS warmed to 37.5° C. to the construct.

In addition, coated but unseeded samples are used to provide insight into material degradation over time. This, combined with the load-strain data collected during dynamic mechanical conditioning, provides an assessment of how quickly load is being transferred to the vessel substitute. It is expected that many of the substrate designs perform well in that the substitute vessels have acceptable burst strengths (i.e., equivalent or better than saphenous vein, 1680 mm Hg), and no cell apoptosis is observed.

EXAMPLE 7

In Vivo Evaluation of Blood Vessel Substitutes

This Example describes the in vivo evaluation of blood vessel substitutes of the invention.

In order to prepare the blood vessel substitutes for implantation, an endothelial cell layer is added to the blood vessel substitute as previously described (Hirai et al. (1994) *ASAIO J.* 40(3):M383-8). Endothelial cells, isolated from Fisher 344 rats are multiplied in culture, suspended in growth medium and allowed to attach to the inner circumference of the blood vessel substitute. It is expected that the surrounding host tissue forms a neo-adventitia around the blood vessel substitute. Alternatively, the outer circumference of the vessel substitute may be coated with a cold mixed solution of aorta fibroblasts from Fisher 344 rats and acid-solved type I collagen (Koken Corp., Tokyo, Japan) prior to implantation (Weinberg & Bell (1986) *Science* 231(4736):397-400).

The Fisher 344 rat animal model is extensively utilized and well accepted in transplantation research because it circumvents the immunological barrier between graft and host (Katayama et al. (1994) *Cell Transplant.* 3 Suppl. 1:S39-41); (Reinecke et al. (1999) *Circulation* 100(2):193-202; Saxena et al. (1999) *Tissue Eng.* 5(6):525-32).

The dimensions of the blood vessel substitutes are ~2.7 mm outer diameter and 18 mm length. One blood vessell substitute is implanted in each of 30 rats, and the animals euthanized at different time points as discussed below.

The procedure is based on those carried out for vascular grafting (Bartels & van der Lei (1988) *Lab. Anim.* 22(2):12-6; Isik et al. (1994) *Transplantation* 58(11):1246-51; Dardik et al. (1999) *J. Vasc. Surg.* 29(1):157-67). The abdomen of an isofluorane-anesthetized rat is shaved and disinfected. The aorta is exposed through a midline abdominal incision. After ligation of the iliolumbar branches, a 20-mm segment of the infrarenal aorta is dissected free from surrounding tissue and the vena cava. The segment is clamped at both ends and resected. All vessel ends are rinsed in heparin solution (1 unit/ml saline, Sigma, St. Louis, Mo.). The resected aorta segment is stored at 4° C. in PBS.

Interpositional grafting of the 18-mm long vessel substitute is performed with end-to-end anastomosis using 9-0 nylon sutures. The clamps are removed and hemostasis is secured by gentle pressure for 1 minute. Patency is determined by direct visual inspection for arterial pulsation in the graft area. The abdomen is closed with Dexon 4-0 sutures after saline irrigation.

For each blood vessel substitute, a control is implanted in a second rat using the same surgical techniques. The control is the harvested aorta segment removed during the blood vessel substitute implantation procedure (homograft).

The blood vessel substitutes and the corresponding controls are removed at intervals of 1 day, 7 days, 3 months, 6 months, and 12 months. 3 experimental and control animals are evaluated at each time point. The earlier time points are chosen to screen for short-term graft failures (L'Heureux et al. (1998) *FASEB J.* 12(1)47-56), while the longer time points monitor long-term functionality, viability, and the remodeling of cellular and extracellular components of the vessel substitute upon in vivo stimulation.

At the time of removal, the rats are anesthetized and the abdominal aorta exposed. The vessel substitute are inspected for patency by a combination of visual inspection of: (1) lateral pulsations; (2) the presence of visible intraluminal thrombus; (3) the presence of prograde flow in the distal region; and (4) the presence of pulsatile flow after distal arteriotomy. The rat is then sacrificed using on overdose of pentobarbitone. Following whole body intracardial perfusion with sterile saline solution and 10% neutral buffered formalin, the vessel substitute and a control section is removed and embedded for histological examination.

Sections (5-micrometer thickness) are stained using a combination of Verhoff's stain (Elastic Stain Kit, Richard-Allan Scientific, Kalamazoo, Mich.) and phosphotungstic acid haematoxylin (PTAH) for the differentiation of SMC from extracellular substance. Staining protocols will be identical to those used previously used (Redwood et al. (1999) *J. Anat.* 195(pt 3):407-12). Quantitative morphological analysis of the histological sections is carried out using a digital imaging system. Several measurements are made at 5 locations along the tissue substitute length: lumen diameter, intimal thickness, medial thickness, and total wall thickness. Total cross-sectional area of the lumen, intima, and media is calculated from these measurements. Measurements are also taken 1 mm beyond the anastomoses to identify possible problematic areas in terms of hyperplasia formation. Means are calculated for each feature.

A comparison of the intimal thickness of the vessel substitute to that of the homograft provides an assessment of the presence of hyperplasia. Immunolabeling may be used to locate the SMCs and identify the separate layers using the histological stains. Primary antibodies to α-smooth muscle cell actin (monoclonal mouse antihuman antibody, DAKO, Carpinteria, Calif.), desmin (monoclonal mouse antihuman antibody, DAKO) and von Willebrand factor (VWF, polyclonal rabbit antihuman antibody, DAKO) are used, based on previously used procedures (Qin et al. (2001) *J. Pathol.* 195 (5):604-8). Vectastain Elite ABC Kit (Vecta Laboratories, Burlingame Calif.) secondary antibodies are used, and sections are visualized using DAB and AEC (Dako Corporation, Carpinteria Calif.) on a Nikon Microphot-SA microscope.

A MANOVA with the variables vessel wall thickness and intimal layer thickness is used to evaluate the results. If results show that one variable dominates the analysis, then individual t-tests are used to assess the relative change of each variable and its significance.

EXAMPLE 8

Microfiber Scaffolds for Forming Skeletal Muscle Substitutes

This Example describes the use of microfiber arrays that mimic the arrangement of muscle fibers in skeletal muscle to make the skeletal muscle substitutes of the invention. A schematic representation of skeletal muscle tissue is shown in FIG. 9.

Previous attempts to tissue-engineer skeletal muscle have not yet lead to a sufficiently contractile muscle graft, mainly because of a lack of cell orientation or a high ratio of biomaterial to tissue. Arrays of parallel-oriented polymer microfiber were investigated for potential use as scaffolds to tissue-engineer skeletal muscle. Several questions were addressed: (1) Can muscle cells be cultured on polymer microfibers? If yes, will the cells align parallel to the fibers? (2) Is it possible to merge cell layers of neighboring fibers? If yes, what is the optimal fiber spacing in order to achieve cell alignment with the lowest possible content of foreign material? (3) Can sheets of parallel-oriented, contractile cells be created? Can such constructs survive for an extended period of time (10 weeks)?

C2C12-myoblast cells, cultured on laminin-coated polypropylene-fibers, formed up to 50 micrometer-thick layers of longitudinally aligned cells. Four different groups of fiber spacing (30 to 35 micrometer, 50 to 55 micrometer, 70 to 75 micrometer, and 90 to 95 micrometer) were evaluated. Complete cell sheets formed between fibers that were spaced 55 micrometer apart or less; larger spacings led to no or incomplete sheets. C2C12-cells seeded onto a 10 mm×20 mm-fiber array, formed a contractile cell sheet that was kept alive in vitro for 70 days. Larger 3-dimensional scaffolds may be created by arranging fibers in several layers or by stacking of cellular sheets, as shown in FIG. 10.

A. Materials and Methods

Fiber Fabrication: Microfibers were made by using a heat-draw method. Polypropylene granules (melt index 800, Aldrich, Milwaukee, Wis.) were heated in a 50 ml beaker until the melting point was reached. Fibers were drawn around a test tube mounted to the shaft of a motor-driven lab stirrer (700-5400, Barnant Barrington, Ill.). The fibers could be produced in a diameter range from 0.5 to several hundred micrometers, depending on melting temperature and shaft rotation speed. Fibers between 10 and 15 micrometer in diameter were used in this study.

Assembly of Fiber Arrays: Frames (outer dimensions: 14.4 mm×22.4 mm, window: 5 mm×10 mm) were cut from 178-micrometer thick mylar sheets (Fralock, Canoga Park, Calif.) using a $CO_2$-laser cutter (M25, Universal Laser Systems Inc., Scottsdale, Ariz.) in conjunction with a CAD program (Corel Draw 9, Corel Corporation, Ottawa, Canada). The frames were coated on one side with a 25-micrometer thick adhesive layer. The microfibers were assembled into 2-dimensional arrays using a custom apparatus (FIG. 2). Polypropylene microfibers were strung between teeth of two opposite-facing lice combs. By adjusting the positions of the combs on slide rails, the distances between adjacent microfibers could be controlled. The microfibers were sandwiched between the sticky sides of two mylar frames to keep the fibers stationary. Before use, frames with fibers were first immersed in a detergent solution (RBS 35, Pierce, Rockford, Ill.) for 30 minutes, rinsed in distilled water twice, and dried in air, protected from dust. The frames were then irradiated from each side with UV light for 30 min and kept in a sterile container until usage.

Cell Culture: C2C12 mouse myoblast cells, strain C3H, were purchased from the American Tissue Type Culture Collection (ATCC; Rockville, Md.). The growth medium used was Dulbecco's modified Eagle's medium (DMEM) with 4 mM L-glutamine, 1.5 g/L sodium bicarbonate and 4.5 g/L glucose, (D 5796, Sigma, St. Louis, Mo.), supplemented with 10% fetal bovine serum (FBS; Hyclone, Logan, Utah), 25 mM HEPES, 1 mM sodium pyruvate, 100 U/ml penicillin, and 100 microgram/ml streptomycin (all Sigma St. Louis, Mo.). For inducing differentiation, FBS was replaced by 10% adult horse serum (HS; Hyclone, Logan, Utah). C2C12 cells were cultured in T75 culture flasks (Corning Inc., Corning, N.Y.) in a humidified incubator (37° C., 5% $CO_2$).

Cell Seeding: Cleaned and sterilized frames were placed in 35-mm plastic Petri dishes (Easy Grip™, Becton Dickinson, Franklin Lakes, N.J.) containing 3.5 ml of laminin-1 solution (50 microgram/ml, Sigma, St. Louis, Mo.) in Dulbecco's phospate buffered saline (DPBS, without Ca/Mg, pH 7.4) Mediatech, Inc., Herndon, Va.). The frames were incubated at 4° C. overnight. Non-coated control frames were incubated in DPBS without laminin content. Undifferentiated C2C12 cells in log-phase were suspended in culture medium, adjusted to the desired cell concentration ($3 \times 10^5$ cells/ml, if not stated otherwise), and pipetted into 35-mm Petri dishes. Immediately afterwards, the frames were removed from the laminin solution, gently rinsed in DPBS, and placed into the dishes with the myoblast suspension. After 30 minutes incubation (37° C., 5% $CO_2$), the frames were transferred into other Petri dishes, each containing culture medium.

Culturing C2C12 Cells on Single Fibers: In order to evaluate adherence and growth of C2C12-myoblast cells on polymer fibers, seven frames each with five fibers at a distance of more than 1 mm from each other were prepared. Five frames were coated with laminin; two were left uncoated. All frames were seeded with C2C12 cells, transferred into Petri dishes containing culture medium, and incubated. Images were taken using an inverted microscope (TMS, Nikon, Inc., Melville, N.Y.); 10× phase objective) in conjunction with a CCD camera and imaging software (Photometrics Cool-SNAPcf, RS Image 1.7.3, Roper Scientific, Trenton, N.J.). The number of attached cells per fiber was counted. To monitor cell growth, the myoblast-seeded arrays were kept in culture for 21 days. The medium was replaced every third day. Cell growth and thickness of the cell layer around the fiber was documented daily. After 21 days in culture the constructs were fixed (4% paraformaldehyde, 20 minutes) and embedded in resin (Technovit 8100, Heraeus Kulzer GmbH, Wehrheim, Germany). 4-micrometer thick cross sections and longitudinal sections were cut and stained with hematoxylin and eosin using standard procedures.

Testing Fiber Spacing: To see if it was possible to merge cell layers of neighboring fibers when in close proximity to each other, and if so, what the maximal distance for fusion to occur would be, frames each containing one pair of fibers in precise spacing were prepared. Fiber spacing was measured using an upright microscope (Microphot SA, Nikon, Inc., Melville, N.Y.) in conjunction with imaging software (Image Pro Plus 3.0, Media Cybernetics, Silver Spring, Md.). Frames with fibers in 30-35 micrometer, 50-55 micrometer, 70-75 micrometer, or 90-95 micrometer spacing were selected (five frames for each spacing group). After cleaning and sterilizing, the frames were incubated in 50 microgram/ml laminin-1 solution as described above. The frames were then placed in two 100-mm Petri dishes, each containing 25 ml of a C2C12-cell suspension. After 30 minutes incubation, the frames were transferred into 100-mm dishes with 25 ml culture medium. Each dish contained four frames, one frame of each spacing group. The culture medium was changed every third day. Cell layer thickness and sheet formation were examined daily.

For histological evaluation, one frame with three fibers at 85 micrometer spacing was prepared, coated with laminin as described above and seeded with C2C12-myoblasts. After 21 days, the frame was fixed in 4% paraformaldehyde for 20 minutes and embedded in resin. Cross sections and longitudinal sections were cut from areas where a sheet including all three fibers had formed. Sections were stained with hematoxylin and eosin following standard procedures.

Creating a Large Cell Sheet: To create a larger muscle sheet, polypropylene fibers (at approximately 20 to 100 micrometer spacing) were fixed between two frames with an inner window of 10 mm×20 mm. The fibers were coated with laminin-1, seeded with C2C12 cells ($10^6$ cells/ml), and immersed in 50 ml culture medium in a 100-mm Petri dish. The medium was changed every third day and the cell sheet was examined in an inverted microscope. After 35 days, the growth medium was replaced with differentiation medium over a period of 7 days to induce increased cell fusion. The cells were then fed with growth medium again. After 70 days in culture, the cell sheet was fixed, embedded, sectioned and stained as above.

B. Results

Creating Cell Layers Around Single Fibers: Only a small number of cells (<4 cells per fiber) adhered to the non-coated fibers. Cell adherence was significantly increased for the laminin-coated fibers with approximately 40 cells per mm of fiber in relatively even distribution. Within the first hour of cultivation, cells changed shape from spherical to humped and started to spread out along the fiber surface. A continuous cell layer surrounded each fiber 24 to 48 hours later. Layer thickness increased steadily to approximately 25 to 40 micrometer, on some fibers up to 50 micrometer at days 12 to 14 of culture. The layers consisted mostly of single cells. Subsequently, the cell layers thickened only slightly. As observed by phase contrast microscopy, the cells appeared to be well aligned in parallel to the fiber axis. Fixed cross sections show cells arranged in 4 to 6 layers with the fiber in the center.

Testing Fiber Spacing: Seeding resulted in approximately 10 attached cells per mm of fiber length. Cells spread and multiplied as observed in the single-fiber experiment. All five 30 to 35 micrometer gaps were fully closed between day 4 and day 5 after seeding; the 50 to 55 micrometer gaps were filled with a complete cell sheet between day 23 and day 28 after seeding. All gaps of 70 micrometer and larger were either not or only partially closed after 28 days (end of the experiment). Cells appeared longitudinally aligned to the fiber axis in the 30 to 35 micrometer gaps and the 50 to 55 micrometer gaps and slightly angled in the partially closed areas of the gaps larger than 70 micrometer. Cross sections show that the sheet thickness was approximately 25 micrometer. Longitudinal sections demonstrate fused myotubes and single cells in parallel alignment.

Large Cell Sheet: The seeding resulted in approximately 30 to 40 cells per mm fiber length. Within one week, the 20 to 30 micrometer-gaps between the fibers were completely filled with sheets of single cells. The 50 to 100 micrometer gaps started to fill from the frame edge; most of these gaps became fully closed before the end of the experiment. However, a few holes remained in the center of the largest gaps. Some neighboring cells spontaneously fused and formed small myotubes. The number and size of myotubes increased significantly after replacing growth medium with differentiation medium. First contractions were observed at day 46 of culture. At first, the contracting areas were small and the contractions irregular. Over time, the number of contracting myotubes increased; the myotubes became longer and thicker, and the contractions became more vigorous. The largest myotubes were about 2.5 to 3 mm long and 20 micrometer in diameter. Myotubes that were adjacent to fibers slid along the fiber surface during contraction. Areas with small myotubes and single cells were found in between contracting large myotubes. Fixed and stained cross sections of the cell-fiber construct depict an approximately 150-micrometer thick sheet of cells with the polymer fibers located in the upper third of the construct.

The results show that myoblast cells attach to micron-diameter polymer fibers, pre-treated with laminin. Although cell attachment of C2C12 cells on laminin-coated flat surfaces has been characterized previously (Schuler & Sorokin (1995) *J. Cell Sci.* 108:3795), it was not clear how the high curvature of the fibers would influence cell binding. When uncoated fibers were used, cell attachment was almost non-existent, indicating the importance of surface modification with attachment proteins. The effect of extracellular matrix (ECM) proteins on cell attachment has been studied extensively (Morla & Mogford (2000) *Biochem. Biophys. Res. Commun.* 272:298; Dexter et al. (2001) *J. Biomed. Mater. Res.* 56:222; Balcells & Edelman (2002) *J. Cell Physiol.* 191:155). Laminin was chosen to coat the fibers because it not only promotes cell attachment and cell growth but also the formation of myotubes, an important structural feature of differentiated muscle (Vachon et al. (1996) *J. Cell Biol.* 134:1483).

The method of cell seeding used was sufficient for attaching cells in relatively even distribution to the fibers. It was possible to increase the seeding density by using a more highly concentrated cell suspension, or by placing frames onto a dense layer of cells that had settled (but not attached) to the bottom of a Petri dish. The fact that the thickness increase of cell layers around single fibers slowed down after reaching a certain limit can be explained by the rising number of differentiated, non-dividing cells in the inner layers. The differentiation of inner cells is most likely triggered by impaired diffusion of nutrients and cell-cell interactions. Interestingly, a few dividing cells often remained present at the surface of the outer cell layers.

Given the results of the single fiber experiment, in which cell layers grew between 25 to 40 micrometer (occasionally 50 micrometer) thick, it was expected that fiber spacings of at least 50 to 80 micrometer could be bridged by C2C12 cells. Instead, only in the 30 to 35 micrometer group and in the 50 to 55 micrometer group was complete cell-sheet formation observed within the duration of the experiment. The reason might lie in the static culture conditions, leading to insufficient diffusion of nutrients and metabolites in the gaps between cell layers, which then stimulated differentiation and decreased the number of dividing cells. This could be circumvented by placing the cultures onto a shaker or by using a bioreactor to ensure proper exchange of media components.

Using parallel fiber arrays, larger sheets of contracting skeletal muscle can be created and kept alive for an extended period of time. Over 10 weeks, the cell sheet grew to a thickness of 150 micrometer. This is in contrast to the performance of C2C12 cells on the bottom of culture dishes, forming monolayers that detach in irregular patches of 1 to 2 mm after 3 to 10 days, and eventually disintegrate (Dennis et al. (2001) *Am. J. Physiol.* 280:C288). These differences might be explained by the fact that in the Petri dish cultures, myocytes are mostly in contact with the surface of the substrate, whereas in the fiber-arrays the majority of cell interaction is with other cells. The cell-cell bond is most likely stronger than the cell-plastic bond. Since myoblast cells formed a complete circular cell layer around the fibers within one to two days after seeding, a separation of the cell layer from the fibers is impossible.

It was observed that myotubes increased in length and thickness over the course of the experiment, resulting in stronger contractions. This enhancement over time might be explained by the fact that contracting myotubes strain other areas that thereby become stimulated to fuse. In some areas, groups of single, non-contracting cells were observed. It is not clear yet if these cells have retained their ability to divide, similar to satellite cells in natural skeletal muscle.

Most myotubes were well aligned along the longitudinal axis. Cross sectional images show an unstructured cell sheet, unlike natural muscle. This was not surprising, since only one cell type was used in this study. The structural composition of tissues is a complex process involving more than one cell type.

It was noticed that, as the cell sheet became thicker, the fibers located more and more in the upper portion of the construct. This can be explained by the influence of gravity. The weight of the cell layer created pressure above the fibers, resulting in impaired diffusion of nutrients and gases in these zones. The cells might have responded with decreased growth rate or with migration into low-pressure zones (below the fibers). The effect can be minimized by periodically turning the frames over (or rotating them) during culture.

Alternative cell sources may be used to bioengineer muscle substitutes. C2C12 is a permanent cell line, derived from mouse skeletal muscle (Yaffe & Saxel (1977) *Nature* 270: 725; Blau et al. (1985) *Science* 230:758), and was used for this study because of its easy availability and ease of culture. Although C2C12 cells differentiate rapidly, form contractile myotubes, and produce characteristic muscle proteins (Blau et al. (1985) *Science* 230:758), it has been shown that myooids of C2C12 possess less contractility than those from primary skeletal muscle cultures (Dennis et al. (2001) *Am. J. Physiol.* 280:C288). To improve contractility and structure, primary cells from mammalian skeletal muscle, including fibroblasts, may be used.

In this Example, non-degradable material was used. Any foreign, non-contractile, material has a negative impact on contractility of the muscle construct. Ideally, the scaffold guides cell orientation and provides mechanical support, then degrades within a certain time frame, but not before the graft attained sufficient mechanical strength. This might be desirable for the repair of congenital diaphragmatic hernia where the muscle patch must sustain pressure differences between the thoracic and abdominal cavities. Successful studies on the biodegradation of polyglycolic acid (PGA) fiber meshes in tissue-engineered skeletal muscle have been described (Saxena et al. (2001) *Biomed. Mater. Erg.* 11:275).

While the preferred embodiment of the invention has been illustrated and described, it will be appreciated that various changes can be made therein without departing from the spirit and scope of the invention.

The embodiments of the invention in which an exclusive property or privilege is claimed are defined as follows:

1. An implantable medical device intended for implantation to a target tissue, said implantable medical device comprising a scaffold comprising two or more arrays of microfibers, the two or more arrays being oriented in regularly spaced, parallel layers,
    wherein each array consists of a plurality of regularly spaced, parallel microfibers, the spacing between the microfibers being between 40 and 60 micrometers,
    wherein at least one spacer is provided to separate the two or more arrays into the regularly spaced, parallel layers,
    wherein the scaffold is designed to mimic the configuration of one or more structural elements in the target tissue, and
    wherein the microfibers are prepared from one or more polymers having a modulus comparable to or slightly greater than that of one or more of the structural elements in the target tissue.

2. An implantable medical device intended for implantation to a target tissue, comprising a tubular scaffold, said scaffold comprising two or more arrays of microfibers, the two or more arrays being oriented in regularly spaced, concentric layers,
    wherein each array consists of a regularly spaced, helically wound microfiber, the spacing between adjacent microfibers being between 40 and 60 micrometers,
    wherein longitudinal spacers are provided to separate the two or more arrays into the regularly spaced, concentric layers,
    wherein the scaffold is designed to mimic the configuration of one or more structural elements in the target tissue, and
    wherein the microfibers are prepared from one or more polymers having a modulus comparable to or slightly greater than that of one or more structural elements in the target tissue.

3. The device of claim 1 or 2, wherein the microfibers have a diameter between about 1 micrometer and about 20 micrometers.

4. The device of claim 1 or 2, wherein the microfibers have a diameter between about 1 micrometer and about 15 micrometers.

5. The device of claim 1 or 2, wherein the microfibers have a diameter between about 1 micrometer and about 6 micrometers.

6. The device of claim 1 or 2, wherein the spacing between the layers of the arrays is between about 10 micrometers and about 200 micrometers.

7. The device of claim 1 or 2, wherein the spacing between the layers of the arrays is between about 60 micrometers and about 160 micrometers.

8. The device of claim 1 or 2, wherein the spacing between the layers of the arrays is between about 80 micrometers and about 120 micrometers.

9. The device of claim 1 or 2, wherein the microfibers are coated with a cell adhesion-enhancing agent.

10. The device of claim 9, wherein the cell adhesion-enhancing agent is selected from the group consisting of collagen, laminin, and fibronectin.

11. The device of claim 1 or 2 further comprising cells cultured on the scaffold to form a target tissue substitute.

12. The device of claim 11, wherein the microfibers comprise a biodegradable polymer that gradually transfers load from the scaffold portion of the target tissue substitute to the cell or tissue portion of the target tissue substitute.

13. The device of claim 12, wherein the biodegradable polymer is selected from the group consisting of a poly-L-lactic acid/polycaprolactone co-polymer, a poly-caprolactone/poly-caprolactone-co-glycolide/poly-hydroxybutyrate-co-hydroxyvalerate/urethane co-polymer, degradable polyurethane, and polyglycolic acid.

14. The device of claim 1, wherein the target tissue is a muscle tissue, wherein an array of microfibers is arranged to mimic the configuration of muscle fibers in the muscle tissue.

15. The device of claim 14, wherein the muscle tissue is skeletal muscle tissue.

16. The device of claim 14, wherein the muscle tissue is cardiac muscle tissue.

17. The device of claim 14, wherein the scaffold comprises between 2 and 20 arrays.

18. The device of claim 14, further comprising cells cultured on the scaffold to form a muscle substitute.

19. The device of claim 18, wherein the cells comprise muscle cells.

20. The device of claim 19, wherein the cells further comprise fibroblasts.

21. The device of claim 1, wherein the target tissue is cartilage tissue, and wherein an array of microfibers is arranged to mimic the configuration of collagen fibers in fibrous cartilage tissue.

22. The device of claim 21, further comprising cells cultured on the scaffold to form a cartilage substitute.

23. The device of claim 22, wherein the cells comprise chondrocytes.

24. The device of claim 23, wherein the cells further comprise fibroblasts.

25. The device of claim 1, wherein the target tissue is a mitral heart valve,
wherein the scaffold comprises a plurality of arrays of microfibers, and
wherein the plurality of arrays of microfibers is arranged to mimic the configuration of collagen fibers in the mitral heart valve.

26. The device of claim 25, further comprising cells cultured on the scaffold to form a mitral heart valve substitute.

27. The device of claim 26, wherein the cells comprise at least one of interstitial valvular cells, fibroblasts, smooth muscle cells, and endothelial cells.

28. The device of claim 26, wherein the cells further comprise fibroblasts.

29. The device of claim 2, wherein the target tissue is esophageal tissue,
wherein the scaffold comprises at least two arrays of microfibers,
wherein a first array of microfibers is arranged to mimic the configuration of the muscle fibers in the circumferential layer of the muscularis externa of the esophagus, and
wherein a second array of microfibers is arranged to mimic the configuration of the muscle fibers in the longitudinal layer of the muscularis externa of the esophagus.

30. The device of claim 29, further comprising cells cultured on the scaffold to form an esophagus substitute.

31. The device of claim 30, wherein the cells comprise muscle cells.

32. A method for forming a target tissue substitute, comprising:
(a) determining the modulus of one or more structural elements in the target tissue;
(b) forming a scaffold comprising two or more arrays of microfibers, the two or more arrays being oriented in regularly spaced, parallel layers,
wherein each array consists of a plurality of regularly spaced, parallel microfibers, the spacing between the microfibers being between 40 and 60 micrometers,
wherein at least one spacer is provided to separate the two or more arrays into the regularly spaced, parallel layers,
wherein the microfibers in one of the arrays are aligned in parallel or at a defined angle with respect to the microfibers in at least one other of the arrays, and
wherein the scaffold is designed to mimic the configuration of one or more structural elements in the target tissue; and
(c) culturing cells on the scaffold to produce a target tissue substitute.

33. A method for forming a tubular target tissue substitute, comprising:
(a) determining the modulus of one or more structural elements in the target tissue;
(b) forming a scaffold comprising two or more arrays of microfibers, the two or more arrays being oriented in regularly spaced, concentric layers,
wherein each array consists of a regularly spaced, helically-wound microfiber, the spacing between the adjacent microfibers being between 40 and 60 micrometers,
wherein longitudinal spacers are provided to separate the two or more arrays into the regularly spaced, concentric layers,
wherein the microfibers in one of the arrays of microfibers are aligned at a defined angle with respect to the microfibers in at least one other of the arrays, and
wherein the scaffold is designed to mimic the configuration of one or more structural elements in the target tissue; and
(c) culturing cells on the scaffold to produce a target tissue substitute.

34. The method of claim 32 or 33, wherein the microfibers have a diameter between about 1 micrometer and about 20 micrometers.

35. The method of claim 32 or 33, wherein the microfibers have a diameter between about 1 micrometer and about 15 micrometers.

36. The method of claim 32 or 33, wherein the microfibers have a diameter between about 1 micrometer and about 6 micrometers.

37. The method of claim 32 or 33, wherein the spacing between the arrays is between about 10 micrometers and about 200 micrometers.

38. The method of claim 32 or 33, wherein the spacing between the arrays is between about 60 micrometers and about 160 micrometers.

39. The method of claim 32 or 33, wherein the spacing between the arrays is between about 80 micrometers and about 120 micrometers.

40. The method of claim 32 or 33, wherein the microfibers comprise a biodegradable polymer that gradually transfers load from the scaffold portion of the target tissue substitute to the cell or tissue portion of the target tissue substitute.

41. The method of claim 40, wherein the biodegradable polymer is selected from the group consisting of a poly-L-lactic acid/polycaprolactone co-polymer, a poly-caprolactone/poly-caprolactone-co-glycolide/poly-hydroxybutyrate-co-hydroxyvalerate/urethane co-polymer, degradable polyurethane, and polyglycolic acid.

42. The method of claim 32 or 33, wherein the microfibers of the arrays are coated with a cell adhesion-enhancing agent.

43. The method of claim 42, wherein the cell adhesion-enhancing agent is selected from the group consisting of collagen, laminin, and fibronectin.

44. The method of claim 32 or 33, wherein in step (c) the cells are cultured on the scaffold in the presence of dynamic mechanical conditioning.

45. The method of claim 1, wherein the target tissue is a muscle tissue, and wherein the arrays of microfibers are designed to mimic the configuration of muscle fibers in the muscle tissue.

46. The method of claim 45, wherein the target tissue is skeletal muscle.

47. The method of claim 45, wherein the target tissue is cardiac muscle.

48. The method of claim 45, wherein the cells comprise muscle cells.

49. The method of claim 48, wherein the cells further comprise fibroblasts.

50. The method of claim 45, wherein the scaffold comprises between 2 and 20 arrays.

51. The method of claim 32, wherein the target tissue is cartilage tissue, and wherein one or more of the arrays of microfibers is designed to mimic the configuration of collagen fibers in fibrous cartilage tissue.

52. The method of claim 51, wherein the cells comprise chondrocytes.

53. The method of claim 52, wherein the cells further comprise fibroblasts.

54. The method of claim 32, wherein the target tissue is mitral heart valve tissue, and wherein the arrays of microfibers are designed to mimic the configuration of collagen fibers of the mitral heart valve.

55. The method of claim 54, wherein the cells comprise at least one of interstitial valvular cells, smooth muscle cells, and endothelial cells.

56. The method of claim 55, wherein the cells further comprise fibroblasts.

57. The method of claim 33, wherein the target tissue is esophageal tissue,
wherein the scaffold comprises at least two arrays of microfibers,
wherein a first array of microfibers is designed to mimic the configuration of muscle fibers in the circumferential layer in the muscularis externa of the esophagus, and
wherein a second array of microfibers is designed to mimic the configuration of muscle fibers in the longitudinal layer in the muscularis externa of the esophagus.

58. The method of claim 57, wherein the cells comprise muscle cells.

59. An implantable medical device intended for implantation to a target tissue,
said implantable medical device comprising a tubular scaffold comprising two or more arrays of microfibers, the two or more arrays being oriented in regularly spaced, concentric layers,
wherein each array consists of a regularly spaced, helically wound microfiber, the spacing between adjacent microfibers being between 40 and 60 micrometers,
wherein longitudinal spacer fibers are provided to separate the two or more arrays into the regularly spaced, concentric layers,
wherein the scaffold is designed to mimic the configuration of one or more structural elements in an arterial blood vessel, and
wherein the arrays of microfibers are prepared from one or more polymers having a modulus comparable to or slightly greater than that of elastin in the medial layer of an arterial blood vessel.

60. The device of claim 59, wherein the scaffold comprises between 2 and 25 arrays.

61. The device of claim 59, further comprising cells cultured on the scaffold to form a blood vessel substitute.

62. The device of claim 61, wherein the cells comprise smooth muscle cells.

63. The device of claim 62, wherein the cells further comprise endothelial cells.

64. The device of claim 61, wherein the blood vessel substitute comprises three arrays and has a burst pressure of more than 1500 mm Hg after 2 weeks of culture in the absence of mechanical conditioning.

65. A method for forming a blood vessel substitute, comprising:
(a) forming a tubular scaffold comprising two or more arrays of microfibers, the two or more arrays being oriented in regularly spaced concentric layers,
wherein each array consists of a regularly spaced, helically wound microfiber, the spacing between the adjacent microfibers being between 40 and 60 micrometers,
wherein longitudinal spacer fibers are provided to separate the two or more arrays into the regularly spaced, concentric layers,
wherein the scaffold is designed to mimic the configuration of elastin in the medial layer of an arterial blood vessel, and
wherein the arrays of microfibers are formed from one or more polymers having a modulus comparable to or slightly greater than that of elastin in the medial layer of an arterial blood vessel; and
(b) culturing cells on the scaffold to produce the blood vessel substitute.

66. The method of claim 65, wherein the cells comprise smooth muscle cells.

67. The method of claim 66, wherein the cells further comprise endothelial cells.

68. The method of claim 65, wherein the scaffold comprises between 2 and 25 arrays.

69. The method of claim 65, wherein the blood vessel substitute comprises three arrays and has a burst pressure of more than 1500 mm Hg after 2 weeks of culture in the absence of mechanical conditioning.

* * * * *

UNITED STATES PATENT AND TRADEMARK OFFICE
CERTIFICATE OF CORRECTION

PATENT NO. : 7,622,299 B2  Page 1 of 1
APPLICATION NO. : 10/374755
DATED : November 24, 2009
INVENTOR(S) : Sanders et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 938 days.

Signed and Sealed this

Twenty-sixth Day of October, 2010

David J. Kappos
*Director of the United States Patent and Trademark Office*